US012563651B2

(12) United States Patent
Patukuri et al.

(10) Patent No.: US 12,563,651 B2
(45) Date of Patent: Feb. 24, 2026

(54) METHODS AND APPARATUS TO SUPPLY POWER TO LED CIRCUITRY

(71) Applicant: Texas Instruments Incorporated, Dallas, TX (US)

(72) Inventors: Raja Reddy Patukuri, Bengaluru (IN); Anand Hariraj Udupa, Bengaluru (IN); Aravind Miriyala, Bengaluru (IN); Sandeep Oswal, Bengaluru (IN); Rajat Agarwal, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 157 days.

(21) Appl. No.: 18/228,454

(22) Filed: Jul. 31, 2023

(65) Prior Publication Data

US 2024/0206034 A1 Jun. 20, 2024

(30) Foreign Application Priority Data

Dec. 14, 2022 (IN) .............................. 202241072156

(51) Int. Cl.
| | |
|---|---|
| *H05B 45/347* | (2020.01) |
| *H05B 45/3725* | (2020.01) |
| *H05B 45/44* | (2020.01) |
| *A61B 5/00* | (2006.01) |

(52) U.S. Cl.
CPC ....... *H05B 45/347* (2020.01); *H05B 45/3725* (2020.01); *H05B 45/44* (2020.01); *A61B 5/0059* (2013.01)

(58) Field of Classification Search
CPC .. H05B 45/347; H05B 45/3725; H05B 45/44; H05B 45/375; A61B 5/0059; A61B 2560/0209; A61B 5/02433; A61B 5/02438; A61B 5/14542; A61B 5/14552; A61B 5/681
See application file for complete search history.

(56) References Cited

U.S. PATENT DOCUMENTS

| | | | | |
|---|---|---|---|---|
| 8,294,375 B2 * | 10/2012 | Lee | ......................... | H05B 45/46 |
| | | | | 345/212 |
| 8,390,262 B2 * | 3/2013 | Chang | .................... | H05B 45/38 |
| | | | | 315/250 |
| 2003/0117087 A1 * | 6/2003 | Barth | ..................... | H05B 45/12 |
| | | | | 315/307 |
| 2009/0289559 A1 * | 11/2009 | Tanaka | ................. | H05B 45/347 |
| | | | | 315/307 |
| 2012/0081016 A1 | 4/2012 | Wu et al. | | |

* cited by examiner

*Primary Examiner* — Daniel D Chang
(74) *Attorney, Agent, or Firm* — Xianghui Huang; Frank D. Cimino

(57) ABSTRACT

An example apparatus includes: driver circuitry having a first terminal and a second terminal; and voltage control circuitry having a first terminal and a second terminal, the first terminal of the voltage control circuitry coupled to the first terminal of the driver circuitry, the second terminal of the voltage control circuitry coupled to the second terminal of the driver circuitry, the voltage control circuitry configured to supply an LED supply voltage.

20 Claims, 9 Drawing Sheets

METHODS AND APPARATUS TO SUPPLY POWER TO LED CIRCUITRY

CROSS-REFERENCE TO RELATED APPLICATION

This patent application claims the benefit of and priority to IN Provisional Patent Application Serial No. 202241072156 filed Dec. 14, 2022, which is hereby incorporated herein by reference in its entirety.

TECHNICAL FIELD

This description relates generally to driver circuitry and, more particularly, to methods and apparatus to supply power to LED circuitry.

BACKGROUND

A light emitting diode (LED) is an electrical component capable of emitting light. An LED includes an anode and a cathode. The anode of an LED may be coupled to a supply voltage, with the cathode of the LED being coupled to a voltage less than the supply voltage. In such a configuration, the LED is forward biased. LEDs emit light responsive to being forward biased and supplied with an electrical current. In some applications, designers effectively use LEDs as light sources, visual indicators, absorption sensors, flashlights, cameras, backlights, displays, etc. As LEDs become increasingly common and popular, incentives for designers to drive LEDs efficiently have greatly increased.

SUMMARY

For methods and apparatus to supply power to LED circuitry, an example apparatus includes driver circuitry having a first terminal and a second terminal; and voltage control circuitry having a first terminal and a second terminal, the first terminal of the voltage control circuitry is coupled to the first terminal of the driver circuitry, the second terminal of the voltage control circuitry is coupled to the second terminal of the driver circuitry, and the voltage control circuitry is configured to supply an LED supply voltage.

BRIEF DESCRIPTION OF THE DRAWINGS

The same reference numbers or other reference designators are used in the drawings to designate the same or similar (functionally and/or structurally) features.

DETAILED DESCRIPTION

Figure 1:
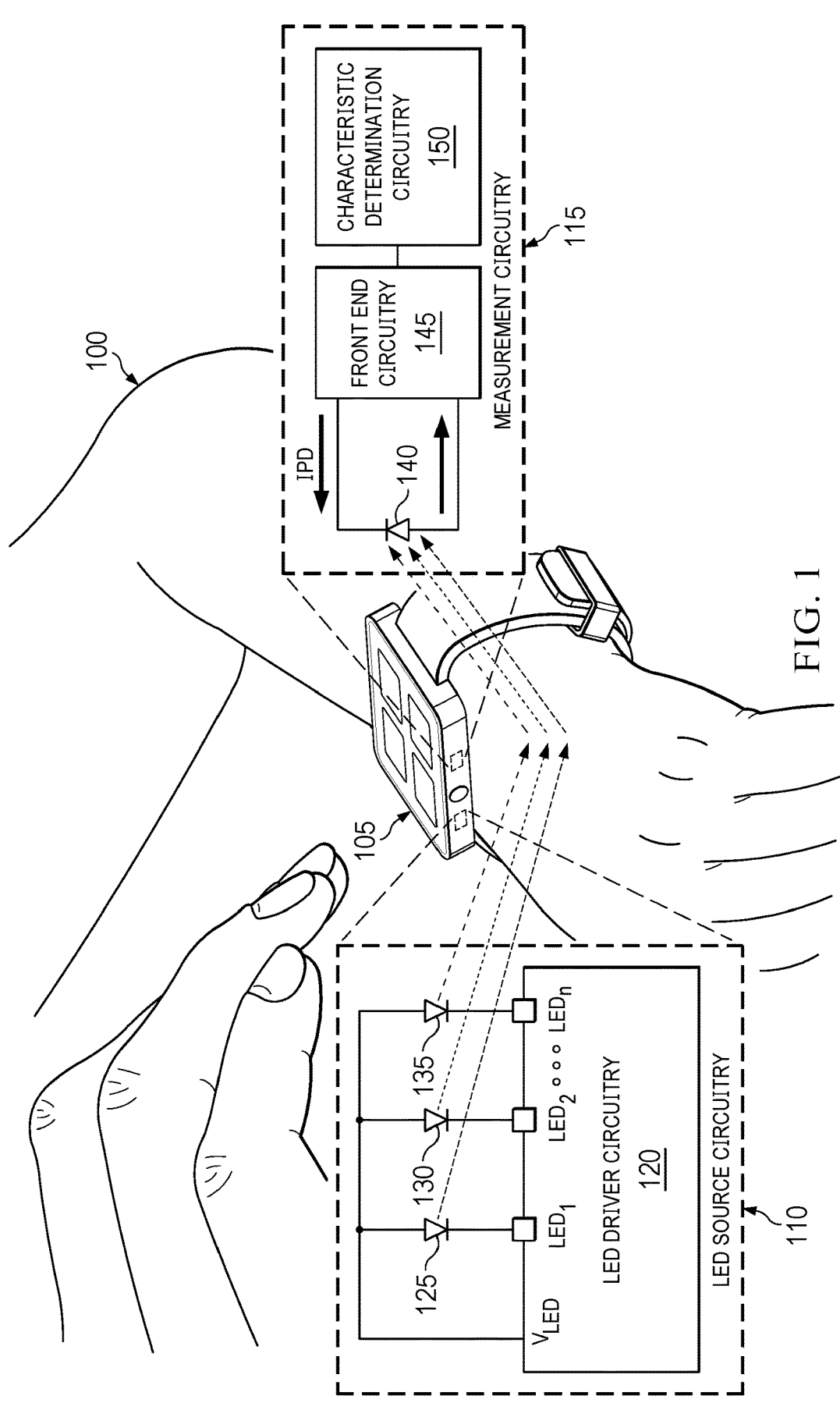
FIG. 1 is a block diagram of an example watch including LED source circuitry and measurement circuitry, the LED source circuitry to emit light to induce a current in the measurement circuitry based on characteristics of a user.

The drawings are not necessarily to scale. Generally, the same reference numbers in the drawing(s) and this description refer to the same or like parts. Although the drawings show regions with clean lines and boundaries, some or all of these lines and/or boundaries may be idealized. In reality, the boundaries and/or lines may be unobservable, blended and/or irregular.

LEDs emit light responsive to LED driver circuitry forward biasing and supplying current to the LEDs. LED driver circuitry forward biases an LED by supplying an LED supply voltage to the anode and a relatively lower voltage to the cathode of an LED. In such a configuration the LED is forward biased, which drives a current through the LED.

LED driver circuitry controls an amount of light the LED emits by controlling an amount of current flowing through the LED. An LED emits more light as the current flowing through the LED increases. However, increasing the current flowing through the LED increases power consumption of the LED driver circuitry and a headroom voltage of the LED driver circuitry.

The headroom voltage results from components of the LED driver circuitry coupled to the cathode of the LED and the current flowing through the LED. As current flows through the LED, impedances and parasitic resistances of components coupled to the cathode of the LED create the headroom voltage. The headroom voltage increases as the current flowing through the LED increases. In some devices, the headroom voltage may increase to a voltage that occupies a relatively large portion of the LED supply voltage. In some such devices, the headroom voltage may increase enough to prevent the LED from being forward biased.

Designers account for such headroom voltages by selecting an LED supply voltage capable of preventing a worst case headroom voltage over multiple applications, for example. The current flowing through the LED decreases as the headroom voltage approaches the worst case headroom voltage. The worst case headroom voltage prevents the LED from being sufficiently forward biased, such as to limit current flowing through the LED. However, increasing the LED supply voltage to account for the worst case headroom voltage increases power consumption. In some devices, such as user specific devices, a headroom voltage of the LED driver circuitry, for a particular use case, may be substantially less than the worst case headroom voltage. In such devices, the LED driver may not be operating as efficiently as possible.

Examples described herein include methods and apparatus to adjust a supply voltage to LED circuitry responsive to measured headroom voltages. In some described examples, LED driver circuitry determines a modified LED supply voltage based on measured headroom voltages. The LED driver circuitry supplies the modified LED supply voltage to one or more LEDs to decrease power consumption. The LED driver circuitry described herein includes LED current driver circuitry, voltage control circuitry, and switch control circuitry. The current driver circuitry sources a current through one or more LEDs using current source circuitry. The voltage control circuitry determines headroom voltages responsive to the sourced current. The voltage control circuitry determines a modified LED supply voltage based on the headroom voltages. The voltage control circuitry configures a power converter to supply the modified LED supply voltage to LEDs.

Advantageously, the voltage control circuitry decreases the LED supply voltage when the measured headroom voltages are more than and/or approximately equal to the worst case headroom voltage. Advantageously, the voltage control circuitry reduces power consumption by determining an LED supply voltage based on measured headroom voltages.

FIG. 1 is a block diagram illustrating an example user 100 wearing an example watch 105 including example LED source circuitry 110 and example measurement circuitry 115. The user 100 is physically coupled to (e.g., wearing) the watch 105. The watch 105 determines characteristics (e.g., blood oxygen level, heart rate, etc.) of the user 100 using the LED source circuitry 110 and the measurement circuitry 115. In the example of FIG. 1, the LED source circuitry 110 and the measurement circuitry 115 are implemented in the watch 105. However, alternative applications and/or implementations of the LED source circuitry 110 and the measurement circuitry 115 may be used based on the described teachings.

The LED source circuitry 110 is optically coupled to measurement circuitry 115 via the user 100. In the example of FIG. 1, the LED source circuitry 110 includes example LED driver circuitry 120, a first example LED 125, a second example LED 130, and a third (or nth) example LED 135. The LED source circuitry 110 emits light of at least one wavelength onto the user 100. In the example of FIG. 1, the measurement circuitry 115 includes an example photodiode 140, example front end circuitry 145, and example characteristic determination circuitry 150. The measurement circuitry 115 detects the light from the LED source circuitry 110 through the user 100. The measurement circuitry 115 determines characteristics of the user 100 based on characteristics of the light being detected.

In example operation, light from the LED source circuitry 110 traverses a portion of the user 100 (e.g., skin) towards the measurement circuitry 115. In an example, the skin of the user 100 modifies or reflects the light from the LED source circuitry 110, responsive to characteristics of the user 100. For example, some light is lost to absorption. The measurement circuitry 115 determines the characteristics of the user 100 based on the light being detected. In the example of FIG. 1, the user 100 may be considered a medium in which light from the LED source circuitry 110 traverses. Alternatively, the LED source circuitry 110 and the measurement circuitry 115 may be modified using the described teachings to emit and/or receive light through alternative and/or a plurality of mediums. In such alternative examples, the measurement circuitry 115 is modified to determine alternative characteristics/properties of the alternative and/or the plurality of mediums.

The LED driver circuitry 120 has a first terminal coupled to the LEDs 125, 130, 135. The LED driver circuitry 120 has a second terminal ($LED_1$) coupled to the first LED 125. The LED driver circuitry 120 has a third terminal ($LED_2$)

coupled to the second LED 130. The LED driver circuitry 120 has a fourth terminal ($LED_n$) coupled to the third LED 135. The LED driver circuitry 120 supplies an LED supply voltage ($V_{LED}$) to the LEDs 125, 130, 135. The LED driver circuitry 120 sources current through at least one of the LEDs 125, 130, 135. One or more of the LEDs 125, 130, 135 emits light at a given time responsive to the LED driver circuitry 120 supplying an LED supply voltage and sourcing current through the one or more of the LEDs 125, 130, 135. In an example operation to illuminate the first LED 125, the LED driver circuitry 120 supplies the LED supply voltage to the first LED 125 and sources a current through the first LED 125.

The LED driver circuitry 120 determines a (e.g., modified) LED supply voltage based on or responsive to one or more headroom voltages of the LED driver circuitry 120. In an example operation, the LED driver circuitry 120 measures a headroom voltage for each of the LEDs 125, 130, 135 responsive to a "worst case" LED supply voltage. The LED driver circuitry 120 compares the measured headroom voltages to determine the modified LED supply voltage. Advantageously, adjusting the LED supply voltage to the modified LED supply voltage reduces power consumption of the LEDs 125, 130, 135. An example of the LED driver circuitry 120 is described below in further detail in connection with FIG. 2.

The first LED 125 has a first terminal coupled to the LED driver circuitry 120. The first LED 125 has a second terminal coupled to the LED driver circuitry 120. The first LED 125 is optically coupled to the measurement circuitry 115. The first LED 125 emits light of a first wavelength responsive to the LED supply voltage and a current sourced by the LED driver circuitry 120. In some examples, the first LED 125 emits green light. In other examples, the first LED 125 may emit one of red light, blue light, infrared light, etc.

The second LED 130 has a first terminal coupled to the LED driver circuitry 120. The second LED 130 has a second terminal coupled to the LED driver circuitry 120. The second LED 130 is optically coupled to the measurement circuitry 115. The second LED 130 emits light of a second wavelength responsive to the LED supply voltage and a current sourced by the LED driver circuitry 120. In some examples, the second LED 130 emits infrared light. In other examples, the second LED 130 may emit one of red light, blue light, green light, etc.

The third LED 135 has a first terminal coupled to the LED driver circuitry 120. The third LED 135 has a second terminal coupled to the LED driver circuitry 120. The third LED 135 is optically coupled to the measurement circuitry 115. The third LED 135 emits light of a third wavelength responsive to the LED supply voltage and a current sourced by the LED driver circuitry 120. In some examples, the third LED 135 emits red light. In other examples, the first LED 125 may emit one of a red light, a blue light, an infrared light, etc. Alternatively, the LED source circuitry 110 may include one or more LEDs configured to emit one or more wavelengths of light.

The photodiode 140 has a first terminal coupled to the front end circuitry 145. The photodiode 140 has a second terminal coupled to the front end circuitry 145. The photodiode 140 is optically coupled to the LED source circuitry 110. The photodiode 140 detects light emitted by the LEDs 125, 130, 135 reflected through the user 100. The photodiode 140 generates a detection current (IPD) responsive to the reflected light from the LEDs 125, 130, 135. A magnitude of the detection current varies responsive to an intensity of the light detected by the photodiode 140. In some examples, characteristics of the user 100 result in relatively high amounts of light absorption, which reduces an amount of light detected by the photodiode 140. Such an increase in light absorption may correspond to variations in blood oxygen levels, a pulse of a heartbeat, etc. In such examples, the reduction in the amount of light reduces the magnitude of the detection current generated by the photodiode 140. The photodiode 140 supplies the detection current to the front end circuitry 145.

The front end circuitry 145 has a first terminal coupled to the photodiode 140. The front end circuitry 145 has a second terminal coupled to the photodiode 140. The front end circuitry 145 has a third terminal coupled to the characteristic determination circuitry 150. The front end circuitry 145 determines a magnitude of the detection current of the photodiode 140. In some examples, the front end circuitry 145 includes an operational amplifier (not illustrated) to determine the magnitude of the detection current. In such examples, an analog-to-digital converter (ADC) converts an output signal of the operational amplifier to a digital value representative of the magnitude of the detection current. The front end circuitry 145 supplies a value representative of the magnitude of the detection current to the characteristic determination circuitry 150.

The characteristic determination circuitry 150 has a terminal coupled to the front end circuitry 145. The characteristic determination circuitry 150 receives the value representative of the magnitude of the detection current through the photodiode 140 from the front end circuitry 145. The characteristic determination circuitry 150 monitors the detection current over time. The characteristic determination circuitry 150 determines characteristics of the user 100 based on the detection current over time. In some examples, the characteristic determination circuitry 150 uses the detection current induced by green light for heart rate monitoring. In other examples, the characteristic determination circuitry 150 uses the detection currents induced by red and infrared lights for blood oxygen monitoring. Alternatively, the characteristic determination circuitry may be used to determine alternative characteristics of the user 100.

Figure 2:
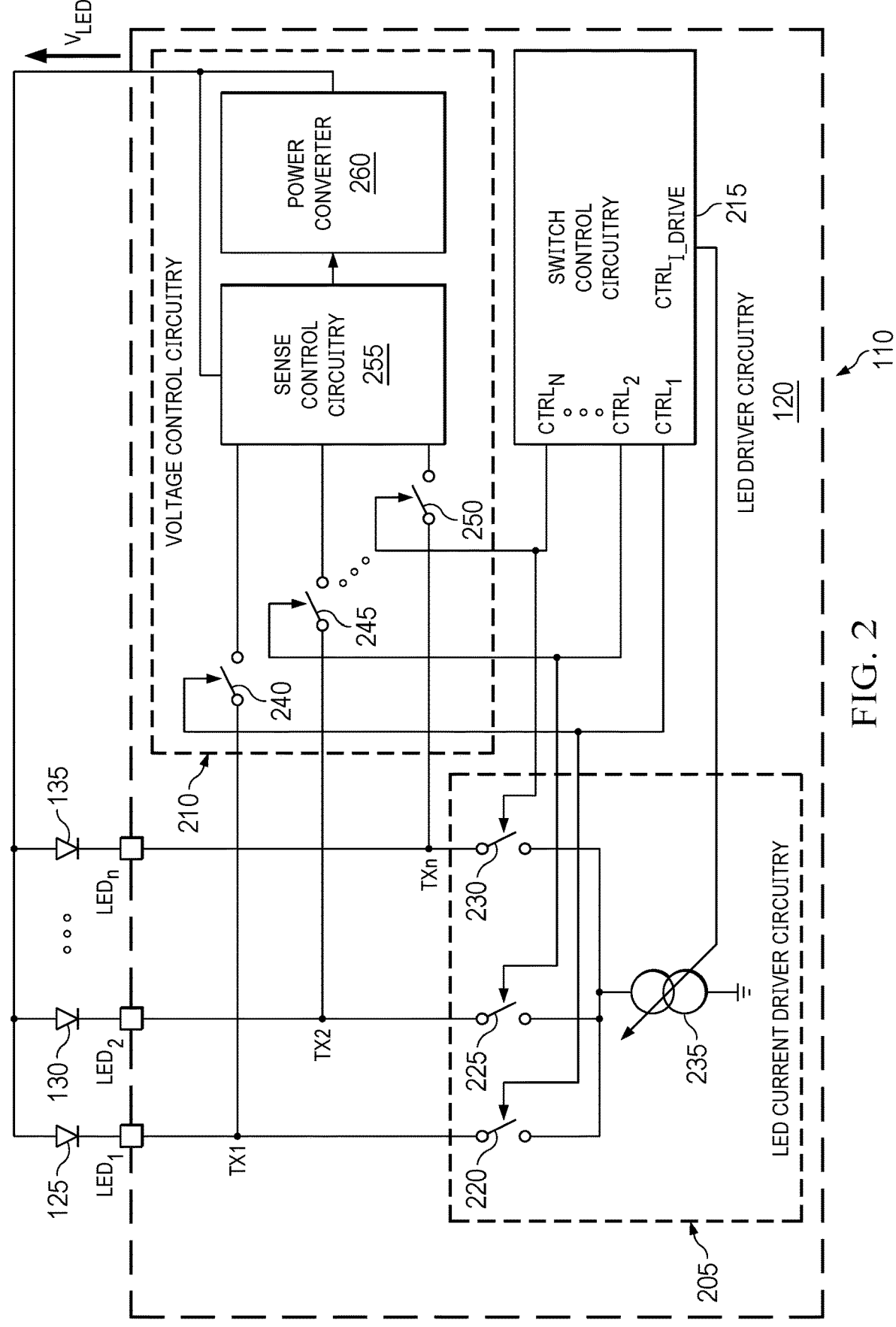
FIG. 2 is a schematic diagram of an example of the LED source circuitry of FIG. 1 including example voltage control circuitry to adjust an LED supply voltage based on headroom voltages of example LED current driver circuitry.

FIG. 2 is a schematic diagram of an example of the LED source circuitry 110 of FIG. 1. In the example of FIG. 2, the LED source circuitry 110 includes the LED driver circuitry 120 of FIG. 1 and the LEDs 125, 130, 135 of FIG. 1. The LED source circuitry 110 supplies an LED supply voltage ($V_{LED}$) to the LEDs 125, 130, 135. At least one of the LEDs 125, 130, 135 emit light responsive to the LED driver circuitry 120 sourcing a current through at least one of the LEDs 125, 130, 135.

The LED driver circuitry 120 is coupled to the LEDs 125, 130, 135. In the example of FIG. 2, the LED driver circuitry 120 includes example LED current driver circuitry 205, example voltage control circuitry 210, and example switch control circuitry 215.

The LED current driver circuitry 205 is coupled to the LEDs 125, 130, 135, the voltage control circuitry 210, and the switch control circuitry 215. In the example of FIG. 2, the LED current driver circuitry 205 includes a first example switch 220, a second example switch 225, a third example switch 230, and example current source circuitry 235. Alternatively, the LED current driver circuitry 205 may include any number of switches corresponding to any number of LEDs to be driven (e.g., the LEDs 125, 130, 135).

The LED current driver circuitry 205 sources a current through at least one of the LEDs 125, 130, 135 responsive to control signals from the switch control circuitry 215. In some examples, a magnitude of the current the LED current driver circuitry 205 is sourcing is adjustable by the switch control circuitry 215. In such examples, the LED current driver circuitry 205 may source a current based on which of the LEDs 125, 130, 135 are to emit light. At least one of the LEDs 125, 130, 135 emit light responsive to the LED current driver circuitry 205 sourcing a current through the at least one of the LEDs 125, 130, 135.

The voltage control circuitry 210 is coupled to the LEDs 125, 130, 135, the LED current driver circuitry 205, and the switch control circuitry 215. In the example of FIG. 2, the voltage control circuitry 210 includes a fourth example switch 240, a fifth example switch 245, a sixth example switch 250, example sense control circuitry 255, and an example power converter 260. The voltage control circuitry 210 determines a headroom voltage for each of the LEDs 125, 130, 135. The voltage control circuitry 210 determines a modified LED supply voltage (e.g., more efficient, application specific, etc.) based on the headroom voltages. The voltage control circuitry 210 supplies the modified LED supply voltage to the LEDs 125, 130, 135. Advantageously, the voltage control circuitry 210 reduces power consumption of the LEDs 125, 130, 135 by determining the modified LED supply voltage based on the headroom voltages.

The switch control circuitry 215 has a first terminal coupled to the switches 220 and 240. The switch control circuitry 215 provides a control signal $CTRL_1$ at the first terminal to control terminals of the switches 220 and 240. The switch control circuitry 215 has a second terminal coupled to the switches 225 and 245. The switch control circuitry 215 provides a control signal $CTRL_2$ at the second terminal to control terminals of the switches 225 and 245. The switch control circuitry 215 has a third terminal coupled to the switches 230 and 250. The switch control circuitry 215 provides a control signal $CTRL_N$ at the third terminal to control terminals of the switches 230 and 250. The switch control circuitry 215 has a fourth terminal coupled to the current source circuitry 235. The switch control circuitry 215 provides a control signal $CTRL_{I\_DRIVE}$ at the fourth terminal to control a current sourced by the current source circuitry 235. The switch control circuitry 215 controls the LED current driver circuitry 205 and the voltage control circuitry 210. The switch control circuitry 215 adjusts the LED current driver circuitry 205. At least one of the LEDs 125, 130, 135 emit light responsive to adjustments to the LED current driver circuitry 205. The voltage control circuitry 210 determines a headroom voltage for one of the LEDs 125, 130, 135 responsive to the switch control circuitry 215 controlling the LED current driver circuitry 205 to couple to and drive the one of the LEDs 125, 130, 135 to emit light. In some examples, the switch control circuitry 215 is instantiated by programmable circuitry executing switch control instructions and/or circuitry configured to perform operations such as those represented by the timing diagram of FIG. 5 and/or the flowchart of FIG. 6.

The first switch 220 has a first terminal coupled to the first LED 125 and the fourth switch 240. The first switch 220 has a second terminal coupled to the switches 225 and 230 and the current source circuitry 235. The first switch 220 has a control terminal coupled to the switch control circuitry 215 and the fourth switch 240. The switch control circuitry 215 controls the first switch 220. The first switch 220 couples the first LED 125 to the current source circuitry 235 when closed (e.g., conducting). The first switch 220 prevents the current source circuitry 235 from sourcing current from the first LED 125 when opened (e.g., non-conducting).

The second switch 225 has a first terminal coupled to the second LED 130 and the fifth switch 245. The second switch 225 has a second terminal coupled to the switches 220 and 230 and the current source circuitry 235. The second switch 225 has a control terminal coupled to the switch control circuitry 215 and the fifth switch 245. The switch control circuitry 215 controls the second switch 225. The second switch 225 couples the second LED 130 to the current source circuitry 235 when closed. The second switch 225 prevents the current source circuitry 235 from sourcing current from the second LED 130 when opened.

The third switch 230 has a first terminal coupled to the third LED 135 and the sixth switch 250. The third switch 230 has a second terminal coupled to the switches 220 and 225 and the current source circuitry 235. The third switch 230 has a control terminal coupled to the switch control circuitry 215 and the sixth switch 250. The switch control circuitry 215 controls the third switch 230. The third switch 230 couples the third LED 135 to the current source circuitry 235 when closed. The third switch 230 prevents the current source circuitry 235 from sourcing current from the third LED 135 when opened.

The current source circuitry 235 has a first terminal coupled to the switches 220, 225, 230. The current source circuitry 235 has a second terminal coupled to a common terminal at which a common potential (e.g., ground) is provided. The current source circuitry 235 has a control terminal coupled to the switch control circuitry 215. The current source circuitry 235 sources a current from the switches 220, 225, 230. The current source circuitry 235 sources a current through one of the LEDs 125, 130, 135 when a corresponding one of the switches 220, 225, 230 are closed. For example, the current source circuitry 235 sources a current from the first LED 125 when the switch control circuitry 215 closes the first switch 220. In such an example, the first LED 125 emits light responsive to the current source circuitry 235 sourcing current through the first LED 125.

In some examples, the switch control circuitry 215 controls a magnitude of the current being sourced by the current source circuitry 235. For example, the switch control circuitry 215 configures the current source circuitry 235 to source a twenty milli-amps (mA) current through the first LED 125 and two hundred milli-amps (mA) through the second LED 130. In such an example, the switch control circuitry 215 controls the current sourced by the current source circuitry 235 by providing the control signal $CTRL_{I\_DRIVE}$ to the current source circuitry 235 to adjust the magnitude of the current and by providing the control signal to close one of the switches 220, 225, and 230220, 225, 230.

In a first configuration of the LED current driver circuitry 205, the first switch 220 is closed and the current source circuitry 235 sources a current from the first LED 125. In the first configuration, a first headroom voltage (TX1) is present at a cathode side of the first LED 125. The first headroom voltage results from a voltage difference across the first switch 220 and the current source circuitry 235.

In a second configuration of the LED current driver circuitry 205, the second switch 225 is closed and the current source circuitry 235 sources a current from the second LED 130. In the second configuration, a second headroom voltage (TX2) is present at a cathode side of the second LED 130. The second headroom voltage results from a voltage difference across the second switch 225 and the current source circuitry 235.

In a third configuration of the LED current driver circuitry 205, the third switch 230 is closed and the current source circuitry 235 sources a current from the third LED 135. In the third configuration, a third headroom voltage (TX3) is present at a cathode side of the third LED 135. The third headroom voltage results from a voltage difference across the third switch 230 and the current source circuitry 235.

The fourth switch 240 has a first terminal coupled to the first LED 125 and the first switch 220. The fourth switch 240 has a second terminal coupled to the sense control circuitry 255. The fourth switch 240 has a control terminal coupled to the switch control circuitry 215 and the first switch 220. The switch control circuitry 215 controls the fourth switch 240. The fourth switch 240, when closed, couples the cathode side of the first LED 125 to the sense control circuitry 255.

The fifth switch 245 has a first terminal coupled to the second LED 130 and the second switch 225. The fifth switch 245 has a second terminal coupled to the sense control circuitry 255. The fifth switch 245 has a control terminal coupled to the switch control circuitry 215 and the second switch 225. The switch control circuitry 215 controls the fifth switch 245. The fifth switch 245, when closed, couples the cathode side of the second LED 130 to the sense control circuitry 255.

The sixth switch 250 has a first terminal coupled to the third LED 135 and the third switch 230. The sixth switch 250 has a second terminal coupled to the sense control circuitry 255. The sixth switch 250 has a control terminal coupled to the switch control circuitry 215 and the third switch 230. The switch control circuitry 215 controls the sixth switch 250. The sixth switch 250, when closed, couples the cathode side of the third LED 135 to the sense control circuitry 255.

The sense control circuitry 255 has a first terminal coupled to the fourth switch 240. The sense control circuitry 255 has a second terminal coupled to the fifth switch 245. The sense control circuitry 255 has a third terminal coupled to the sixth switch 250. The sense control circuitry 255 has a fourth terminal coupled to the power converter 260. The sense control circuitry 255 has a fifth terminal coupled to the LEDs 125, 130, and 135 and the power converter 260. In an example, the sense control circuitry 255 determines (e.g., measures) the headroom voltages, e.g., TX1, TX2, and TX3, of the LED current driver circuitry 205. The sense control circuitry 255 determines a minimum headroom voltage based on the headroom voltages. The sense control circuitry 255 determines the modified LED supply voltage as the LED supply voltage that supports the minimum headroom voltage. The sense control circuitry 255 configures the power converter 260 to supply the modified LED supply voltage to the LEDs 125, 130, 135. An example of the sense control circuitry 255 is described in further detail in connection with FIGS. 3 and 4, below.

The power converter circuitry 260 has a first terminal coupled to the sense control circuitry 255. The power converter circuitry 260 has a second terminal coupled to the LEDs 125, 130, 135 and the sense control circuitry 255. The power converter 260 supplies the LED supply voltage to the LEDs 125, 130, 135. The power converter 260 generates the LED supply voltage responsive to a signal from the sense control circuitry 255, and based on the headroom voltages. An example of the power converter 260 is illustrated and described in further detail in FIG. 3, below.

Figure 3:
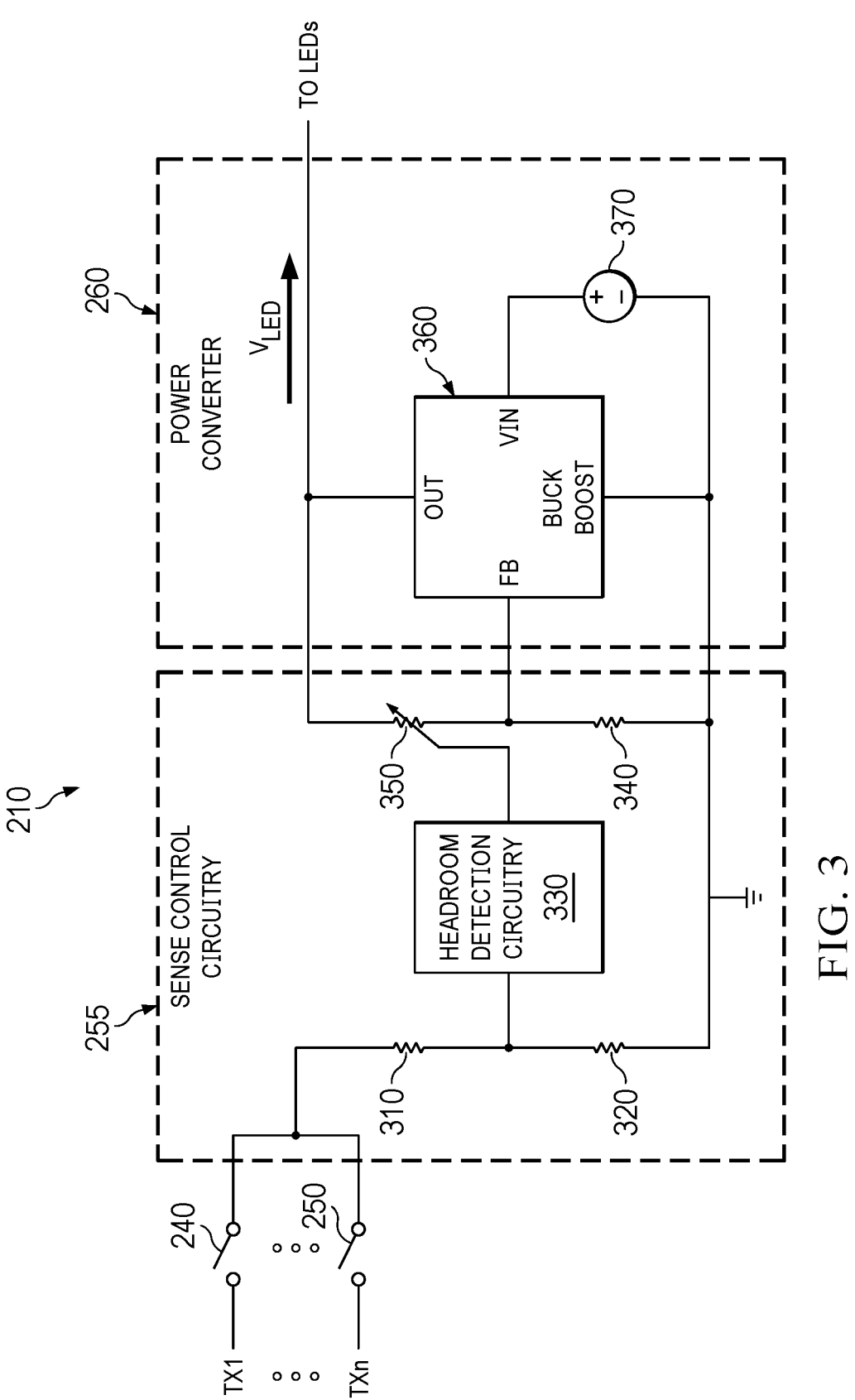
FIG. 3 is a schematic diagram of an example of the voltage control circuitry of FIG. 2 including headroom detection circuitry to determine a minimum headroom voltage of the LED current driver circuitry of FIG. 2.

FIG. 3 is a schematic diagram of an example of the voltage control circuitry 210 of FIG. 2 including the switches 240 and 250 of FIG. 2, the sense control circuitry 255 of FIG. 2, and the power converter 260 of FIG. 2. The sense control circuitry 255 is coupled to the switches 240 and 250 and the power converter 260. In the example of FIG. 3, the sense control circuitry 255 includes a first example resistor 310, a second example resistor 320, example headroom detection circuitry 330, a third example resistor 340, and an example variable resistor 350.

The first resistor 310 has a first terminal coupled to the switches 240 and 250. The first resistor 310 has a second terminal coupled to the second resistor 320 and the headroom detection circuitry 330. The first resistor 310 has a first resistance. The second resistor 320 has a first terminal coupled to the first resistor 310 and the headroom detection circuitry 330. The second resistor 320 has a second terminal coupled to the common terminal that provides the common potential. The second resistor 320 has a second resistance.

In example operation, the resistors 310 and 320 operate as voltage divider circuitry. The resistors 310 and 320 step down a voltage from the switches 240 and 250 based on the resistances of the resistors 310 and 320. In such an example operation, the resistors 310 and 320 create stepped down headroom voltages of the headroom voltages from the switches 240, 245, 250. Advantageously, stepping down the voltage from the switches 240, 245, 250 allows the headroom detection circuitry 330 to implement relatively lower voltage logic. Advantageously, the relatively lower voltage logic can operate at relatively higher speeds. In an alternative example, the sense control circuitry 255 may be modified to remove and/or modify the resistors 310 and/or 320 to implement alternative voltage divider circuitry and/or remove the voltage divider circuitry.

The headroom detection circuitry 330 has a first terminal coupled to the resistors 310 and 320. The headroom detection circuitry 330 has a second terminal coupled to the variable resistor 350. The headroom detection circuitry 330 receives the stepped down headroom voltages at the connected terminals of the resistors 310 and 320. The headroom detection circuitry 330 compares the stepped down headroom voltages and determines a minimum headroom voltage corresponding to the LED current driver circuitry 105 of FIGS. 1 and 2. In such examples, the headroom detection circuitry 330 adjusts a resistance of the variable resistor 350 responsive to the minimum headroom voltage. In other examples, the headroom detection circuitry 330 determines the current being sourced through the LEDs 125, 130, 135 from the switch control circuitry 215 of FIG. 2 and the minimum headroom voltage. In such examples, the headroom detection circuitry 330 adjusts a resistance of the variable resistor 350 based on the current and headroom voltages of the LEDs 125, 130, 135. The headroom detection circuitry 330 configures the power converter 260 to provide a (modified) LED supply voltage responsive to modifying the resistance of the variable resistor 350.

An example of the headroom detection circuitry 330 is illustrated and described in connection with FIG. 4, below. In some examples, the headroom detection circuitry 330 is instantiated by programmable circuitry executing headroom detection instructions and/or circuitry configured to perform operations such as those represented by the flowchart of FIG. 6.

The third resistor 340 has a first terminal coupled to the power converter 260 and the variable resistor 350. The third resistor 340 has a second terminal coupled to the common terminal that provides the common potential. The third resistor 340 has a third resistance. The variable resistor 350 has a first terminal coupled to the power converter 260 and coupled to the LEDs 125, 130, 135. The variable resistor 350 has a second terminal coupled to the power converter 260 and the third resistor 340. The variable resistor 350 has a control terminal coupled to the headroom detection circuitry 330. The headroom detection circuitry 330 controls a resistance of the variable resistor 350.

In an example operation, the third resistor 340 and the variable resistor 350 operate as voltage divider circuitry. The third resistor 340 and the variable resistor 350 generate a feedback voltage based on the resistance of the third resistor 340 and the configured resistance of the variable resistor 350. The third resistor 340 and the variable resistor 350 supply the feedback voltage to the power converter 260, at the connected terminals of the resistors 340 and 350.

In some examples, the sense control circuitry 255 includes alternative circuitry to generate the feedback voltage. For example, the voltage divider circuitry of the resistors 340 and 350 may be replaced with a modified variable resistor. In such an example, the modified variable resistor generates the feedback voltage based on a minimum headroom voltage.

In other examples, the sense control circuitry 255 may include alternative circuitry to control the power converter 260. In such examples, the resistors 340 and 350 may be replaced and/or modified using communication circuitry to control the power converter 260. For example, the power converter 260 may be communicatively coupled to communication circuitry. In such an example, the communication circuitry may utilize a communication protocol (e.g., inter-integrated circuit (I2C), serial peripheral interface (SPI), etc.) to control the power converter 260 to modify the LED supply voltage.

The power converter 260 is coupled to the sense control circuitry 255. The power converter 260 is coupled to the LEDs 125, 130, 135. In the example of FIG. 3, the power converter 260 includes an example buck-boost converter 360 and an example power supply 370. The power converter 260 receives a reference voltage from the sense control circuitry 255. The power converter 260 generates the modified LED supply voltage based on the reference voltage and based on a supply voltage provided by the power supply 370. The power converter 260 supplies the modified LED supply voltage to the LEDs 125, 130, 135.

The buck-boost converter 360 has a supply input (VIN) coupled to the power supply 370. The buck-boost converter 360 has a feedback input (FB) coupled to the third resistor 340 and the variable resistor 350. The buck-boost converter 360 has a reference input coupled to the common terminal that provides the common potential. The buck-boost converter 360 has an output (OUT) coupled to the variable resistor 350 and to the LEDs 125, 130, 135. The buck-boost converter 360 receives the reference voltage at FB. The buck-boost converter 360 receives a supply voltage from the power supply 370 at VIN.

The buck-boost converter 360 generates the LED supply voltage ($V_{LED}$) based on the supply voltage and the reference voltage and provides $V_{LED}$ at OUT. In some examples, the buck-boost converter 360 boosts the supply voltage from the power supply 370 to generate an LED supply voltage greater than the supply voltage. In other examples, the buck-boost converter 360 bucks the supply voltage from the power supply 370 to generate an LED supply voltage less than the supply voltage. The buck-boost converter 360 determines whether to buck or boost the supply voltage responsive to the reference voltage from the sense control circuitry 255. The buck-boost converter 360 generates the modified LED supply voltage responsive to the headroom detection circuitry 330 configuring the variable resistor 350. Alternatively, the power converter 260 may be replaced and/or modified consistent with the teachings described herein to utilize another type of power conversion, such as a buck converter, a boost converter, etc.

The power supply 370 has a first terminal coupled to the buck-boost converter 360. The power supply 370 has a second terminal coupled to the common terminal that provides the common potential. The power supply supplies the supply voltage to the buck-boost converter 360.

Figure 4:
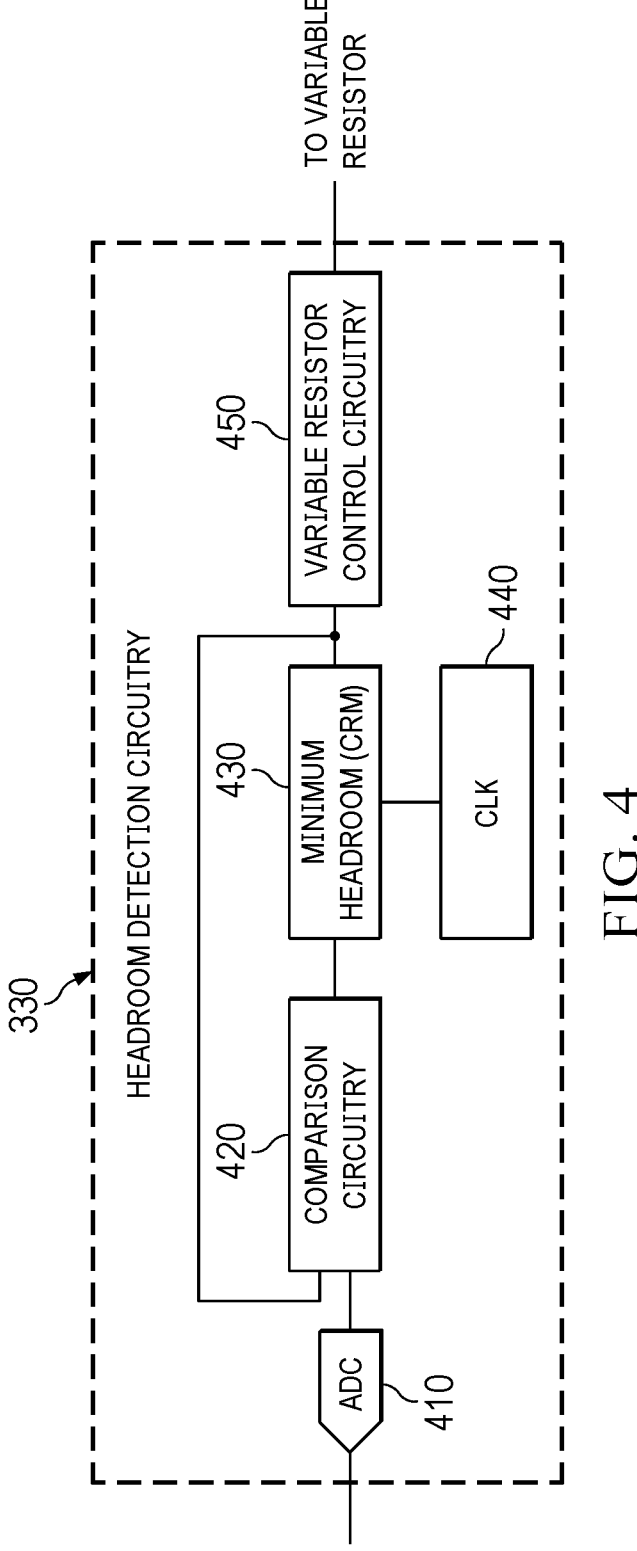
FIG. 4 is a schematic diagram of an example of the headroom detection circuitry of FIG. 3.

FIG. 4 is a block diagram of an example implementation of the headroom detection circuitry 330 of FIG. 3 to improve the LED supply voltage based on headroom voltages of the LEDs 125, 130, 135. The headroom detection circuitry 330 of FIG. 3 may be instantiated (e.g., creating an instance of, bring into being for any length of time, materialize, implement, etc.), at least in part, by programmable circuitry such as a Central Processor Unit (CPU) executing first instructions. Additionally or alternatively, the headroom detection circuitry 330 of FIG. 3 may be instantiated (e.g., creating an instance of, bring into being for any length of time, materialize, implement, etc.), at least in part by, by (i) an Application Specific Integrated Circuit (ASIC) and/or (ii) a Field Programmable Gate Array (FPGA) structured and/or configured in response to execution of second instructions to perform operations corresponding to the first instructions. All of the circuitry of FIG. 3 may, thus, be instantiated at the same or different times. Some or all of the circuitry of FIG. 2 may be instantiated, for example, in one or more threads executing concurrently on hardware and/or in series on hardware. Moreover, in some examples, some or all of the circuitry of FIG. 3 may be implemented by microprocessor circuitry executing instructions and/or FPGA circuitry performing operations to implement one or more virtual machines and/or containers. In the example of FIG. 4, the headroom detection circuitry 330 includes an example ADC 410, example comparison circuitry 420, example minimum headroom register 430, an example clock 440, and example variable resistor control circuitry 450.

The ADC 410 has a first terminal adaptive to be coupled to the resistors 310 and 320 of FIG. 3. The ADC 410 has a second terminal coupled to the comparison circuitry 420. The ADC 410 receives an analog representation of the headroom voltages of the LEDs 125, 130, 135 of FIGS. 1 and 2. The ADC 410 converts the analog representation of the headroom voltage to a digital value representative of the headroom voltage. The ADC 410 supplies the digital value to the comparison circuitry 420. In some examples, the ADC 410 may be a successive approximation register (SAR) ADC. Alternatively, another type of ADC is utilized consistent with the teachings described herein.

The comparison circuitry 420 has a first input coupled to the ADC 410. The comparison circuitry 420 has a second input coupled to the minimum headroom register 430 and the variable resistor control circuitry 450. The comparison circuitry 420 has an output coupled to the minimum headroom register 430. The comparison circuitry 420 receives a first digital value representing the headroom voltage from the ADC 410. The comparison circuitry 420 receives a second digital value representing a current minimum headroom voltage from the minimum headroom register 430. The comparison circuitry 420 compares the first and second digital values to determine the minimum headroom voltage. The comparison circuitry 420 stores the value representing the minimum headroom voltage in the minimum headroom register 430. In an example, the minimum headroom voltage represents the smallest of the measured or detected headroom voltages. In some examples, the comparison circuitry 420 is instantiated, at least in part, by programmable circuitry executing comparison instructions and/or configured to perform operations such as those represented by the flowchart of FIG. 6.

The minimum headroom register 430 has a first input coupled to the comparison circuitry 420. The minimum headroom register 430 has a second input coupled to the clock 440. The minimum headroom register 430 has an output coupled to the comparison circuitry 420 and the variable resistor control circuitry 450. The minimum headroom register 430 stores the value of the minimum headroom voltage from the comparison circuitry 420. The minimum headroom register 430 provides the value representative of the minimum headroom voltage to the comparison circuitry 420 and the variable resistor control circuitry 450. The minimum headroom register 430 utilizes a clock signal from the clock 440 to reduce memory instability. In the example of FIG. 4, the value representing the minimum headroom voltage is stored in the minimum headroom register 430. Alternatively, the headroom detection circuitry 330 may be modified consistent with the teachings described herein to utilize alternative memory and/or circuitry to store a value representing the minimum headroom voltage. In some examples, the minimum headroom register 430 is instantiated, at least in part, by a data register and/or programmable circuitry executing minimum headroom instructions and/or configured to perform operations such as those represented by the flowchart of FIG. 6.

The variable resistor control circuitry 450 has an input coupled to the minimum headroom register 430. The variable resistor control circuitry 450 has an output coupled to the variable resistor 350 of FIG. 3. The variable resistor control circuitry 450 receives the value representing the minimum headroom voltage from the minimum headroom register 430. The variable resistor control circuitry 450 adjusts the resistance of the variable resistor 350 based on the minimum headroom voltage. For example, the variable resistor control circuitry 450 provides a control signal to a control terminal of the variable resistor 350. In some examples, the variable resistor control circuitry 450 is instantiated, at least in part, by programmable circuitry executing variable resistor control instructions and/or configured to perform operations such as those represented by the flowchart of FIG. 6.

In an example operation, at powerup, the power converter 260 of FIG. 2 supplies a default LED supply voltage to the LEDs 125, 130, 135 responsive to the minimum headroom register 430 storing a default value. In some examples, the default value represents a maximum LED supply voltage. The variable resistor control circuitry 450 configures the variable resistor 350 to set the buck-boost converter 360 to generate a default LED supply voltage when the default value is in the minimum headroom register 430.

In such an example operation, the switch control circuitry 215 of FIG. 2 configures the LED current driver circuitry 205 of FIG. 2 to separately source a current through the LEDs 125, 130, 135. The switches 240, 245, 250 of FIGS. 2 and 3 are individually closed by the switch control circuitry 215 as the LED current driver circuitry 205 sources the current through the LEDs 125, 130, 135. In the first example operation of the LED current driver circuitry 205, the switches 220 and 240 is closed (and the other switches are open). During such a configuration the resistors 310 and 320 generate a stepped down headroom voltage proportional to the headroom voltage TX1. The ADC 410 converts the stepped down headroom voltage to a digital value corresponding to the stepped down headroom voltage. The comparison circuitry 420 compares the digital value from the ADC 410 to the default value stored in the minimum headroom register 430. If the digital value from the ADC 410 is less than the default value, the comparison circuitry

420 replaces the default value, in the minimum headroom register 430, with the digital value from the ADC 410.

The switch control circuitry then provides control signals to enable the measurement of headroom voltages TX2 to TXn and the similar comparisons, resulting in the value representing the smallest of the headroom voltages being stored in the minimum headroom register 430. Once the switch control circuitry 215 cycles through all configurations of the LED current driver circuitry 205, the variable resistor control circuitry 450 determines an adjusted LED supply voltage based on the minimum headroom voltage of the minimum headroom register 440. The variable resistor control circuitry 450 determines the adjusted LED supply voltage to be approximately equal to the default LED supply voltage minus at least a portion the minimum headroom voltage.

The variable resistor controller circuitry 450 determines an adjusted feedback voltage of the power converter 260. The power converter 260 generates the adjusted LED supply voltage responsive to the adjusted feedback voltage.

In some examples, the variable resistor controller circuitry 450 applies voltage division with a resistance of the third resistor 340, the adjusted feedback voltage, and the adjusted LED supply. In such examples, the variable resistor controller circuitry 450 determines a resistance of the variable resistor 350 that generates the adjusted feedback voltage.

In other examples, the variable resistor controller circuitry 450 applies the adjusted LED supply voltage and/or the minimum headroom voltage to a look-up table (LUT) to determine a resistance of the variable resistor 350. In such examples, resistances of the LUT are determined using voltage division, as described herein.

In yet another example, the variable resistor controller circuitry 450 uses communication circuitry, which implements a communication protocol, to modify the power converter 260. In such examples, the variable resistor controller circuitry 450 supplies a value representative of the adjusted LED supply voltage to the power converter 260 using a communication protocol.

Advantageously, the buck-boost converter 360 supplies an adjusted LED supply voltage to the LEDs 125, 130, 135 responsive to the variable resistor control circuitry 450 adjusting the variable resistor 350. Advantageously, the headroom detection circuitry 330 configures the variable resistor 350 to reduce power consumption by reducing, whenever possible, the LED supply voltage. For example, the final LED supply voltage is a smallest LED voltage that allows proper operation of all the LEDs of the LED source circuitry 110. Advantageously, adjusting the LED supply voltage based on measured headroom voltages decreases future headroom voltages, which decreases power consumption.

While an example of the headroom detection circuitry 330 of FIG. 3 is illustrated in FIG. 4, one or more of the elements, processes, and/or devices illustrated in FIG. 4 may be combined, divided, re-arranged, omitted, eliminated, and/or implemented in any other way. Further, the ADC 410, the comparison circuitry 420, the minimum headroom register 430, variable resistor control circuitry 450, and/or, more generally, the example headroom detection circuitry 330 of FIG. 4, may be implemented by hardware alone or by hardware in combination with software and/or firmware. Thus, for example, any of the ADC 410, the comparison circuitry 420, the minimum headroom register 430, variable resistor control circuitry 450, and/or, more generally, the example headroom detection circuitry 330, could be implemented by programmable circuitry in combination with machine readable instructions (e.g., firmware or software), processor circuitry, analog circuit(s), digital circuit(s), logic circuit(s), programmable processor(s), programmable microcontroller(s), graphics processing unit(s) (GPU(s)), digital signal processor(s) (DSP(s)), ASIC(s), programmable logic device(s) (PLD(s)), and/or field programmable logic device(s) (FPLD(s)) such as FPGAs. Further still, the example headroom detection circuitry 330 of FIG. 4 may include one or more elements, processes, and/or devices in addition to, or instead of, those illustrated in FIG. 4, and/or may include more than one of any or all of the illustrated elements, processes and devices.

Figure 5:
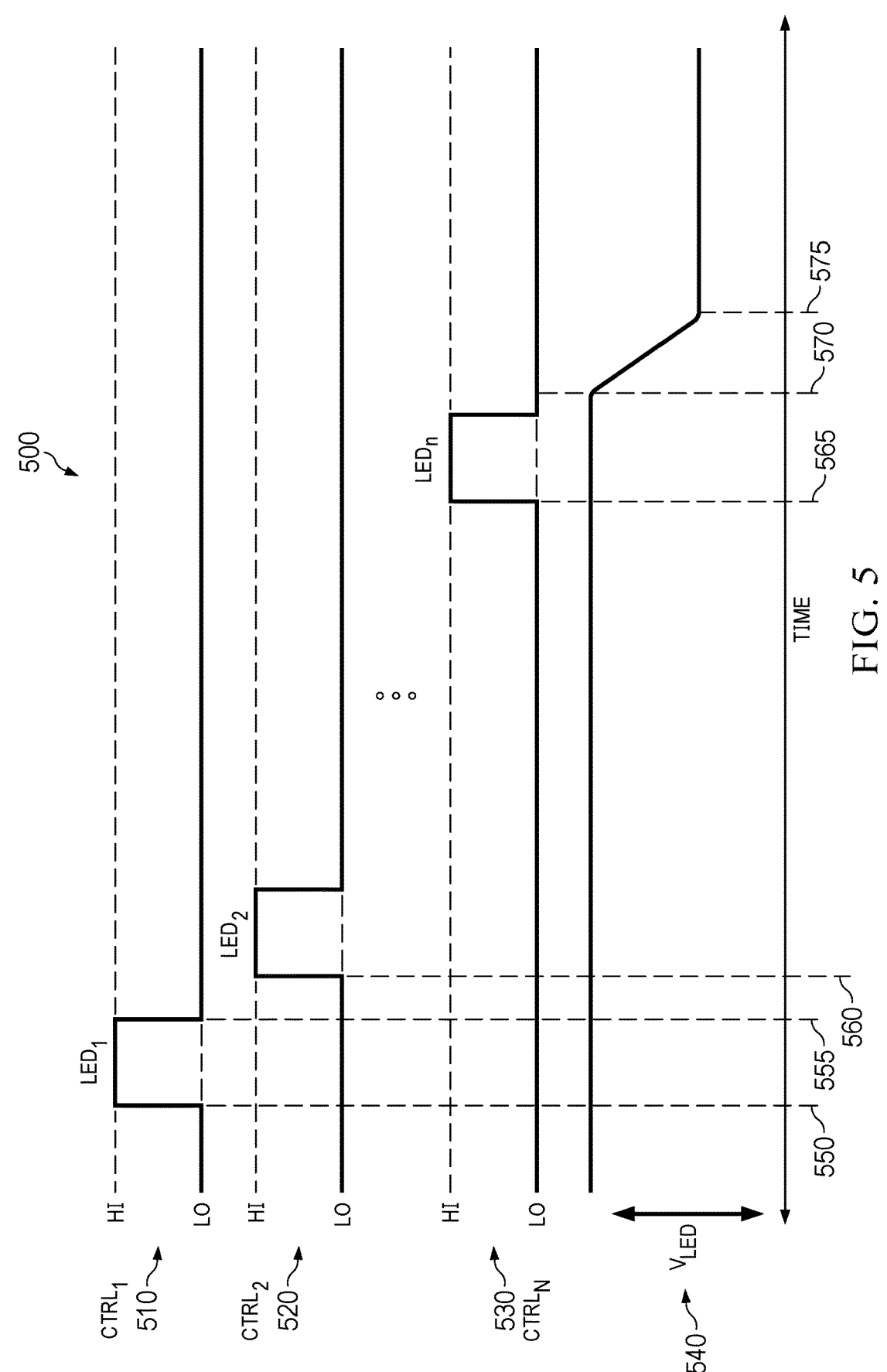
FIG. 5 is a timing diagram of an example operation of the LED source circuitry of FIGS. 1 and 2.

FIG. 5 is a timing diagram 500 of an example operation of the LED source circuitry 110 of FIGS. 1 and 2. In the example of FIG. 5, the timing diagram 500 illustrates a first example switch control signal 510 (e.g., $CTRL_1$), a second example switch control signal 520 (e.g., $CTRL_2$), a third example switch control signal 530 (e.g., $CTRL_N$), and an example LED supply voltage 540 (e.g., (e.g., $V_{LED}$).

The first switch control signal 510 represents a signal from the switch control circuitry 215 of FIG. 2 to control the switches 220 and 240 of FIGS. 2 and 3. When the first switch control signal 510 is a logic high (HI), the switches 220 and 240 are closed. When the first switch control signal 510 is a logic low (LOW), the switches 220 and 240 are open. In some examples, the first LED 125 of FIGS. 1 and 2 emits light when the first switch control signal 510 is a logic high.

The second switch control 520 represents a signal from the switch control circuitry 215 to control the switches 225 and 245 of FIGS. 2 and 3. When the second switch control 520 is a logic high, the switches 225 and 245 are closed. When the second switch control 520 is a logic low, the switches 225 and 245 are open. In some examples, the second LED 130 of FIGS. 1 and 2 emits light when the second switch control 520 is a logic high.

The third switch control signal 530 represents a signal from the switch control circuitry 215 to control the switches 230 and 250 of FIGS. 2 and 3. When the third switch control signal 530 is a logic high, the switches 230 and 250 are closed. When the third switch control signal 530 is a logic low, the switches 230 and 250 are open. In some examples, the third LED 135 of FIGS. 1 and 2 emits light when the third switch control signal 530 is a logic high.

The LED supply voltage 540 represents a voltage that the voltage control circuitry 210 of FIG. 2 supplies to the LEDs 125, 130, 135.

At a first time 550, the first switch control signal 510 transitions from a logic low to a logic high. At the first time 550, the switch control circuitry 215 closes the switches 220 and 240 to turn on the first LED 125. Following the first time 550, the sense control circuitry 255 determines a first headroom voltage of the LED driver circuitry 120 while the first LED 125 emits light. At such a time following the first time 550, the headroom detection circuitry 330 of FIGS. 3 and 4 compares the headroom voltage to the value (e.g., a default value) in the minimum headroom register 430 of FIG. 4. At a second time 555, the first switch control signal 510 transitions from a logic high to a logic low. At the second time 555, the switch control circuitry 215 opens the switches 220 and 240 to turn off the first LED 125.

At a third time 560, the second switch control 520 transitions from a logic low to a logic high. In the example of FIG. 5, the time between the times 555 and 560 allows LED source circuitry 110 to settle. In some examples, the times 555 and 560 may occur at approximately the same time. At the third time 560, the switch control circuitry 215 closes the switches 225 and 245 to turn on the second LED 130. Following the third time 560, the sense control circuitry 255 determines a second headroom voltage of the LED driver circuitry 120 while the second LED 130 emits light. At such a time following the third time 560, the comparison circuitry 420 of FIG. 4 compares the second headroom voltage to the value in the minimum headroom register 430. If the second headroom voltage is less than the first headroom voltage, the comparison circuitry 420 stores a value representative of the second headroom voltage in the minimum headroom register 430.

At a fourth time 565, the third switch control signal 530 transitions from a logic low to a logic high. At the fourth time 565, the switch control circuitry 215 closes the switches 230 and 250 to turn on the third LED 135. Following the fourth time 565, the sense control circuitry 255 determines a third headroom voltage of the LED driver circuitry 120 while the third LED 135 emits light. At such a time following the fourth time 565, the comparison circuitry 420 compares the third headroom voltage to the value of the minimum headroom register 430. If the third headroom voltage is less than the value of the minimum headroom register 430, the comparison circuitry 420 stores a value representative of the third headroom voltage in the minimum headroom register 430.

At a fifth time 570, the variable resistor control circuitry 450 of FIG. 4 configures the variable resistor 350 of FIG. 3 based on the value of the minimum headroom register 430. At the fifth time 570, the value of the minimum headroom register 430 represents the lowest measured headroom voltage from the LEDs 125, 130, 135. Advantageously, the headroom detection circuitry 330 determines a modified LED supply voltage using headroom voltages from a single cycle of the LEDs 125, 130, 135.

Following the fifth time 570, the buck-boost converter 360 of FIG. 3 adjusts the LED supply voltage 540 responsive to the new value of the variable resistor 350. At a sixth time 575, the LED supply voltage 540 settles responsive to an output of the buck-boost converter 360 having settled on a value based on the value of the variable resistor 350. Advantageously, the headroom detection circuitry 330 reduces power consumption responsive to the modified LED supply voltage being lower than a default LED supply voltage.

Figure 6:
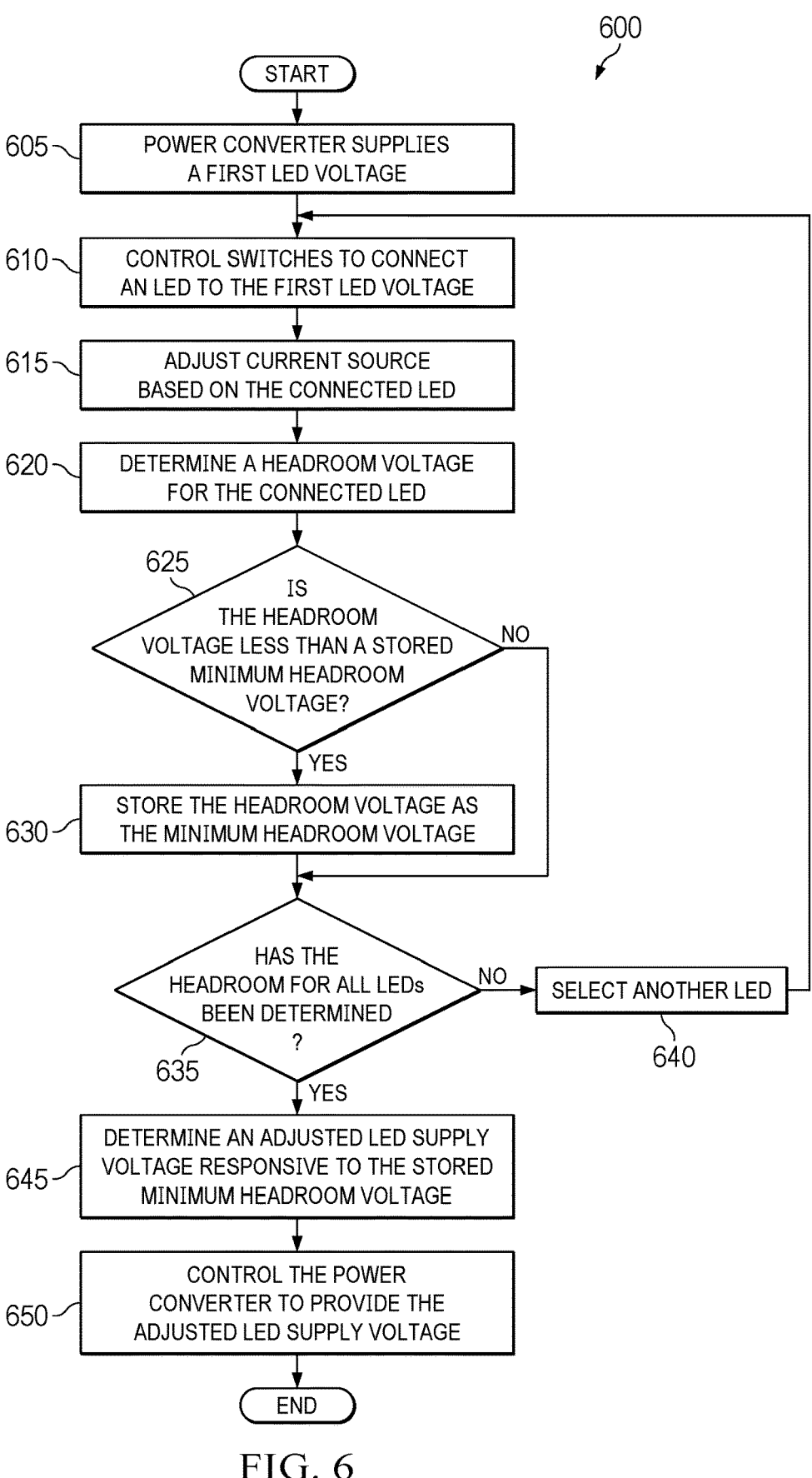
FIG. 6 is a flowchart representative of example operations that may be executed, instantiated, and/or performed using an example of the LED driver circuitry of FIGS. 1 and 2.

FIG. 6 is a flowchart representative of example operations 600 that may be executed, instantiated, and/or performed by the LED driver circuitry 120 of FIGS. 1 and 2 to adjust an LED supply voltage for the LEDs 125, 130, 135 of FIGS. 1 and 2. The example machine-readable instructions and/or the example operations 600 of FIG. 6 begin at Block 605, at which the power converter 260 of FIGS. 2 and 3 supplies a first LED voltage to the LEDs, responsive to a resistance of the variable resistor 350 of FIG. 3 adjusts. In some examples, the variable resistor control circuitry 450 of FIG. 4 configures the variable resistor 350 to a resistance that sets an output of the buck-boost converter 360 of FIG. 3 to a default voltage. The default voltage represents an LED supply voltage that has not been adjusted based on headroom voltages. In such an example, the buck-boost converter 360 boosts the supply voltage from the power supply 370 of FIG. 3.

The switch control circuitry 215 of FIG. 2 controls switches (e.g., the switches 220, 225, 230 of FIGS. 2 and/or 240, 245, 250 of FIGS. 2 and 3) to connect an LED (e.g., the LEDs 125, 130, 135) to the first LED voltage. (Block 610). In some examples, the switch control circuitry 215 generates one or more of the switch control signals 510, 520, 530 of FIG. 5 to control the switches 220, 225, 230 and/or 240, 245, 250. In such examples, the switch control circuitry 215 closes one of the switches 220, 225, 230 to couple the current source circuitry 235 of FIG. 2 to one of the LEDs 125, 130, 135.

The switch control circuitry 215 adjusts the current source circuitry 235 based on the connected LED (e.g., the LED coupled to the current source circuitry 235 at Block 610). (Block 615). In some examples, the current source circuitry 235 sources a different current from each of the LEDs 125, 130, 135 to achieve a target current transfer ratio (CTR). The target current transfer ratio is a ratio of a current through one of the LEDs 125, 130, 135 to the detection current from the photodiode 140 of FIG. 1. In such an example, the switch control circuitry 215 adjusts the current source circuitry 235 based on which of the LEDs 125, 130, 135 are on.

The voltage control circuitry 210 of FIGS. 2 and 3 determines (e.g., detects) a headroom voltage, of the LED driver circuitry 120, for the connected LED. (Block 620). In some examples, the sense control circuitry 255 of FIGS. 2 and 3 is coupled to the LED current driver circuitry 205 of FIG. 2 and one of the LEDs 125, 130, 135 by one of the switches 240, 245, 250. In such examples, headroom detection circuitry 330 samples the headroom voltage at the cathode of the one of the LEDs 125, 130, 135 currently emitting light. For example, the ADC 410 samples a voltage representative of the headroom voltage. In other examples, the sense control circuitry 255 determines the headroom of one of the LEDs 125, 130, 135 and the current sourced by the LED current driver circuitry 205.

The comparison circuitry 420 of FIG. 4 determines if the headroom voltage is less than a stored minimum headroom voltage (e.g., the headroom voltage stored in the minimum headroom register 430 of FIG. 4). (Block 625). In some examples, the comparison circuitry 420 compares the value of the headroom voltage stored in the minimum headroom register 430 to a value of a headroom voltage from the ADC 410 of FIG. 4.

If the comparison circuitry 420 determines that the headroom voltage is less than a stored minimum headroom voltage (e.g., Block 625 returns a result of YES), the comparison circuitry 420 stores the headroom voltage as the minimum headroom voltage in the minimum headroom register 430. (Block 630). In some examples, the comparison circuitry 420 writes a digital value representative of the headroom voltage, from Block 620, to the minimum headroom register 430. In such examples, the digital value is the output of the ADC 410.

The switch control circuitry 215 determines if a headroom voltage has been determined for all LEDs. (Block 635). In some examples, the switch control circuitry 215 determines if the voltage control circuitry 330 has determined headroom voltages for all of the LEDs 125, 130, 135 based on whether all of the LEDs 125, 130, 135 have been turned on. For example, the switch control circuitry 215 would determine that the voltage control circuitry 210 has not determined a headroom voltage until the fifth time 570 of FIG. 5.

If the switch control circuitry 215 determines that a headroom has not been determined for all LEDs (e.g., Block 635 returns a result of NO), the switch control circuitry 215 selects another LED. (Block 640). In some examples, the switch control circuitry 215 selects one of the LEDs 125, 130, 135 that have not been turned on. Control proceeds to return to Block 610 with the selected LED.

If the switch control circuitry 215 determines that a headroom has been determined for all LEDs (e.g., Block 635 returns a result of YES), the sense control circuitry 255 determines an adjusted LED supply voltage responsive to the stored minimum headroom voltage. (Block 645). In some examples, the variable resistor control circuitry 450 of FIG. 4 determines the adjusted the LED supply voltage is approximately equal to the default LED supply voltage minus the minimum headroom voltage. For example, the variable resistor control circuitry 450 determines an adjusted LED supply voltage to be three and a half volts when the default supply voltage is approximately equal to four volts and the minimum headroom voltage is approximately equal to half a volt. In such an example, adjusting the LED supply voltage by half a volt decreases power consumption of the LED driver circuitry by approximately one-eighth.

The sense control circuitry 255 controls the power converter 260 to provide the adjusted LED supply voltage. (Block 650). In some examples, the variable resistor control circuitry 450 configures the power converter 260 to generate the adjusted LED supply voltage by adjusting the variable resistor 350. In such examples, the voltage divider circuitry of the resistors 340 and 350 generates an adjusted feedback voltage, which controls the power converter 260, responsive to the variable resistor control circuitry 450 adjusting the resistance of the variable resistor 350.

In some examples, the variable resistor control circuitry 450 determines the resistance of the variable resistor 350 based on the characteristics of the voltage divider circuitry of the resistors 340 and 350 at the adjusted LED supply voltage. For example, the variable resistor control circuitry 450 adjusts the resistance of the variable resistor 350 to two-hundred and fifty ohms (Ω) when the adjusted LED supply voltage is to be three and a half volts, the resistance of the third resistor 340 is approximately one-hundred ohms, and the power converter 260 generates three and a half volts responsive to a feedback voltage approximately equal to one volt. In such an example, the variable resistor control circuitry 450 uses voltage division to determine the resistance of the variable resistor 350 needs to be two-hundred and fifty ohms when the feedback voltage needs to be approximately one volt.

In other examples, the variable resistor control circuitry 450 determined the resistance of the variable resistor 350 based on predetermined values. For example, the variable resistor control circuitry 450 uses a look-up table (LUT) to determine a resistance that corresponds to the adjusted LED supply voltage and/or the minimum headroom voltage. In such examples, the predetermined values of the LUT are determined using voltage division across the resistors 340 and 350, as described above.

In some other examples, the headroom detection circuitry 330 utilizes communication circuitry (not illustrated) to be communicatively coupled to the power converter 260. In such examples, the headroom detection circuitry 330 utilizes a communication protocol to modify the buck-boost converter 360. Control proceeds to end.

Although example processes are described with reference to the flowchart illustrated in FIG. 6, many other methods of determining a modified LED supply voltage based on headroom voltages may alternatively be used in accordance with teachings of this disclosure. For example, the order of execution of the blocks may be changed, and/or some of the blocks described may be changed, eliminated, or combined. Similarly, additional operations may be included in the manufacturing process before, in between, or after the blocks shown in the illustrated examples.

Flowchart(s) representative of example machine readable instructions, which may be executed by programmable circuitry to implement and/or instantiate the LED driver circuitry 120 of FIGS. 1 and 2 and/or representative of example operations which may be performed by programmable circuitry to implement and/or instantiate the LED driver circuitry 120 of FIGS. 1 and 2, are shown in FIG. 6. The machine readable instructions may be one or more executable programs or portion(s) of one or more executable programs for execution by programmable circuitry such as the programmable circuitry 712 shown in the example processor platform 700 described below in connection with FIG. 7 and/or may be one or more function(s) or portion(s) of functions to be performed by the example programmable circuitry (e.g., an FPGA) described below in connection with FIGS. 8 and/or 9. In some examples, An operation, a task, etc., is carried out and/or performed in an automated manner in the real world responsive to the machine readable instructions. As used herein, "automated" means without human involvement.

The program may be embodied in instructions (e.g., software and/or firmware) stored on one or more non-transitory computer readable and/or machine readable storage medium such as cache memory, a magnetic-storage device or disk (e.g., a floppy disk, a Hard Disk Drive (HDD), etc.), an optical-storage device or disk (e.g., a Blu-ray disk, a Compact Disk (CD), a Digital Versatile Disk (DVD), etc.), a Redundant Array of Independent Disks (RAID), a register, ROM, a solid-state drive (SSD), SSD memory, non-volatile memory (e.g., electrically erasable programmable read-only memory (EEPROM), flash memory, etc.), volatile memory (e.g., Random Access Memory (RAM) of any type, etc.), and/or any other storage device or storage disk. The instructions of the non-transitory computer readable and/or machine readable medium may program and/or be executed by programmable circuitry located in one or more hardware devices, but the entire program and/or parts thereof could alternatively be executed and/or instantiated by one or more hardware devices other than the programmable circuitry and/or embodied in dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a human and/or machine user) or an intermediate client hardware device gateway (e.g., a radio access network (RAN)) that may facilitate communication between a server and an endpoint client hardware device. Similarly, the non-transitory computer readable storage medium may include one or more mediums. Further, although the example program is described with reference to the flowchart(s) illustrated in FIGS. 6, many other methods of implementing the example switch control circuitry 215 of FIG. 2 and/or the headroom detection circuitry 330 of FIGS. 3 and 4 may alternatively be used. For example, the order of execution of the blocks of the flowchart(s) may be changed, and/or some of the blocks described may be changed, eliminated, or combined. Additionally or alternatively, any or all of the blocks of the flow chart may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The programmable circuitry may be distributed in different network locations and/or local to one or more hardware devices (e.g., a single-core processor (e.g., a single core CPU), a multi-core processor (e.g., a multi-core CPU, an XPU, etc.)). For example, the programmable circuitry may be a CPU and/or an FPGA located in the same package (e.g., the same integrated circuit (IC) package or in two or more separate housings), one or more processors in a single machine, multiple processors distributed across multiple servers of a server rack, multiple processors distributed across one or more server racks, etc., and/or any combination(s) thereof.

The machine-readable instructions described herein may be stored in one or more of a compressed format, an encrypted format, a fragmented format, a compiled format, an executable format, a packaged format, etc. Machine readable instructions as described herein may be stored as data (e.g., computer-readable data, machine-readable data, one or more bits (e.g., one or more computer-readable bits, one or more machine-readable bits, etc.), a bitstream (e.g., a computer-readable bitstream, a machine-readable bitstream, etc.), etc.) or a data structure (e.g., as portion(s) of instructions, code, representations of code, etc.) that may be utilized to create, manufacture, and/or produce machine executable instructions. For example, the machine-readable instructions may be fragmented and stored on one or more storage devices, disks and/or computing devices (e.g., servers) located at the same or different locations of a network or collection of networks (e.g., in the cloud, in edge devices, etc.). The machine-readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of computer-executable and/or machine executable instructions that implement one or more functions and/or operations that may together form a program such as that described herein.

In another example, the machine readable instructions may be stored in a state in which they may be read by programmable circuitry, but require addition of a library (e.g., a dynamic link library (DLL)), a software development kit (SDK), an application programming interface (API), etc., in order to execute the machine-readable instructions on a particular computing device or other device. In another example, the machine-readable instructions may need to be configured (e.g., settings stored, data input, network addresses recorded, etc.) before the machine readable instructions and/or the corresponding program(s) can be executed in whole or in part. Thus, machine readable, computer readable and/or machine-readable media, as used herein, may include instructions and/or program(s) regardless of the particular format or state of the machine readable instructions and/or program(s).

The machine-readable instructions described herein can be represented by any past, present, or future instruction language, scripting language, programming language, etc. For example, the machine-readable instructions may be represented using any of the following languages: C, C++, Java, C#, Perl, Python, JavaScript, HyperText Markup Language (HTML), Structured Query Language (SQL), Swift, etc.

As mentioned above, the example operations of FIG. 6 may be implemented using executable instructions (e.g., computer readable and/or machine-readable instructions) stored on one or more non-transitory computer readable and/or machine readable media. As used herein, the terms non-transitory computer readable medium, non-transitory computer readable storage medium, non-transitory machine readable medium, and/or non-transitory machine-readable storage medium are expressly defined to include any type of computer readable storage device and/or storage disk and to exclude propagating signals and to exclude transmission media. Examples of such non-transitory computer readable medium, non-transitory computer readable storage medium, non-transitory machine readable medium, and/or non-transitory machine readable storage medium include optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms "non-transitory computer readable storage device" and "non-transitory machine-readable storage device" are defined to include any physical (mechanical, magnetic and/or electrical) hardware to retain information for a time period, but to exclude propagating signals and to exclude transmission media. Examples of non-transitory computer readable storage devices and/or non-transitory machine-readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer-readable instructions, machine-readable instructions, etc.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements, or actions may be implemented by, e.g., the same entity or object. Additionally, although individual features may be included in different examples or claims, these may possibly be combined, and the inclusion in different examples or claims does not imply that a combination of features is not feasible and/or advantageous.

Figure 7:
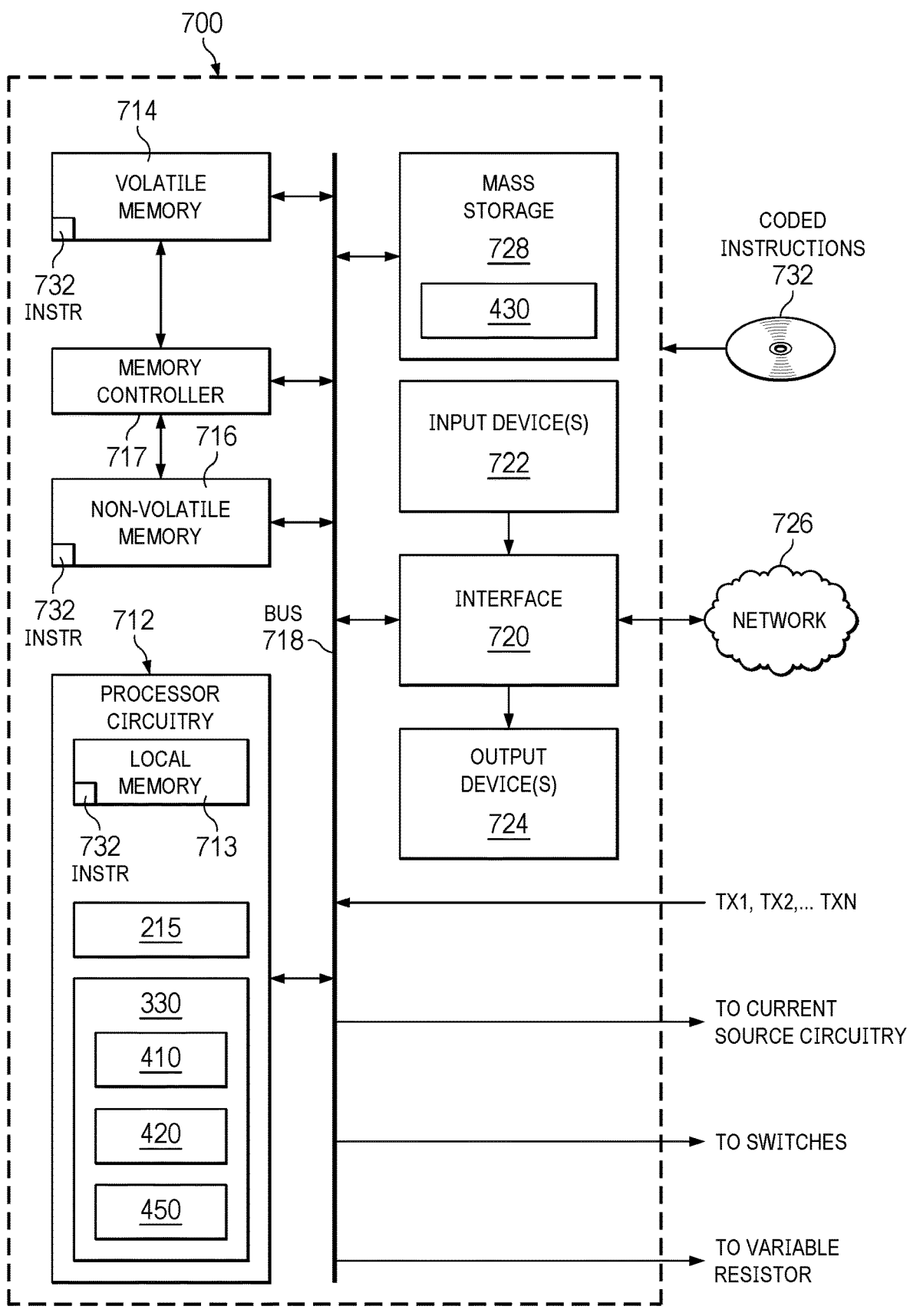
FIG. 7 is a block diagram of an example processing platform including programmable circuitry structured to execute, instantiate, and/or perform the example machine readable instructions and/or perform the example operations of FIG. 6 to implement the LED driver circuitry of FIGS. 1 and 2.

FIG. 7 is a block diagram of an example programmable circuitry platform 700 structured to execute and/or instantiate the example machine-readable instructions and/or the example operations of FIG. 6 to implement the switch control circuitry 215 and/or the headroom detection circuitry 330 of FIG. 4. The programmable circuitry platform 700 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, a headset (e.g., an augmented reality (AR) headset, a virtual reality (VR) headset, etc.) or other wearable device, or any other type of computing and/or electronic device.

The programmable circuitry platform 700 of the illustrated example includes programmable circuitry 712. The programmable circuitry 712 of the illustrated example is hardware. For example, the programmable circuitry 712 can be implemented by one or more integrated circuits, logic circuits, FPGAs, microprocessors, CPUs, GPUs, DSPs, and/or microcontrollers from any desired family or manufacturer. The programmable circuitry 712 may be implemented by one or more semiconductor based (e.g., silicon based) devices. In this example, the programmable circuitry 712 implements the switch control circuitry 215 of FIG. 2, the headroom detection circuitry 330 of FIGS. 3 and 4, the ADC 410 of FIG. 4, the comparison circuitry 420 of FIG. 4, and the variable resistor control circuitry 450 of FIG. 4.

The programmable circuitry 712 of the illustrated example includes a local memory 713 (e.g., a cache, registers, etc.). The programmable circuitry 712 of the illustrated example is in communication with main memory 714, 716, which includes a volatile memory 714 and a non-volatile memory 716, by a bus 718. The volatile memory 714 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 716 may be implemented by flash memory and/or any other desired type of memory device. Access to the main memory 714, 716 of the illustrated example is controlled by a memory controller 717. In some examples, the memory controller 717 may be implemented by one or more integrated circuits, logic circuits, microcontrollers from any desired family or manufacturer, or any other type of circuitry to manage the flow of data going to and from the main memory 714, 716.

The programmable circuitry platform 700 of the illustrated example also includes interface circuitry 720. The interface circuitry 720 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 722 are connected to the interface circuitry 720. The input device(s) 722 permit(s) a user (e.g., a human user, a machine user, etc.) to enter data and/or commands into the programmable circuitry 712. The input device(s) 722 can be implemented by, for example, an audio sensor, a microphone, a camera (still or video), a keyboard, a button, a mouse, a touchscreen, a trackpad, a trackball, an isopoint device, and/or a voice recognition system.

One or more output devices 724 are also connected to the interface circuitry 720 of the illustrated example. The output device(s) 724 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 720 of the illustrated example, thus, typically includes a graphics driver card, a graphics driver chip, and/or graphics processor circuitry such as a GPU.

The interface circuitry 720 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 726. The communication can be by, for example, an Ethernet connection, a digital subscriber line (DSL) connection, a telephone line connection, a coaxial cable system, a satellite system, a beyond-line-of-sight wireless system, a line-of-sight wireless system, a cellular telephone system, an optical connection, etc.

The programmable circuitry platform 700 of the illustrated example also includes one or more mass storage discs or devices 728 to store firmware, software, and/or data. Examples of such mass storage discs or devices 728 include magnetic storage devices (e.g., floppy disk, drives, HDDs, etc.), optical storage devices (e.g., Blu-ray disks, CDs, DVDs, etc.), RAID systems, and/or solid-state storage discs or devices such as flash memory devices and/or SSDs.

The machine readable instructions 732, which may be implemented by the machine readable instructions of FIGS. 6, may be stored in the mass storage device 728, in the volatile memory 714, in the non-volatile memory 716, and/or on at least one non-transitory computer readable storage medium such as a CD or DVD which may be removable.

Figure 8:
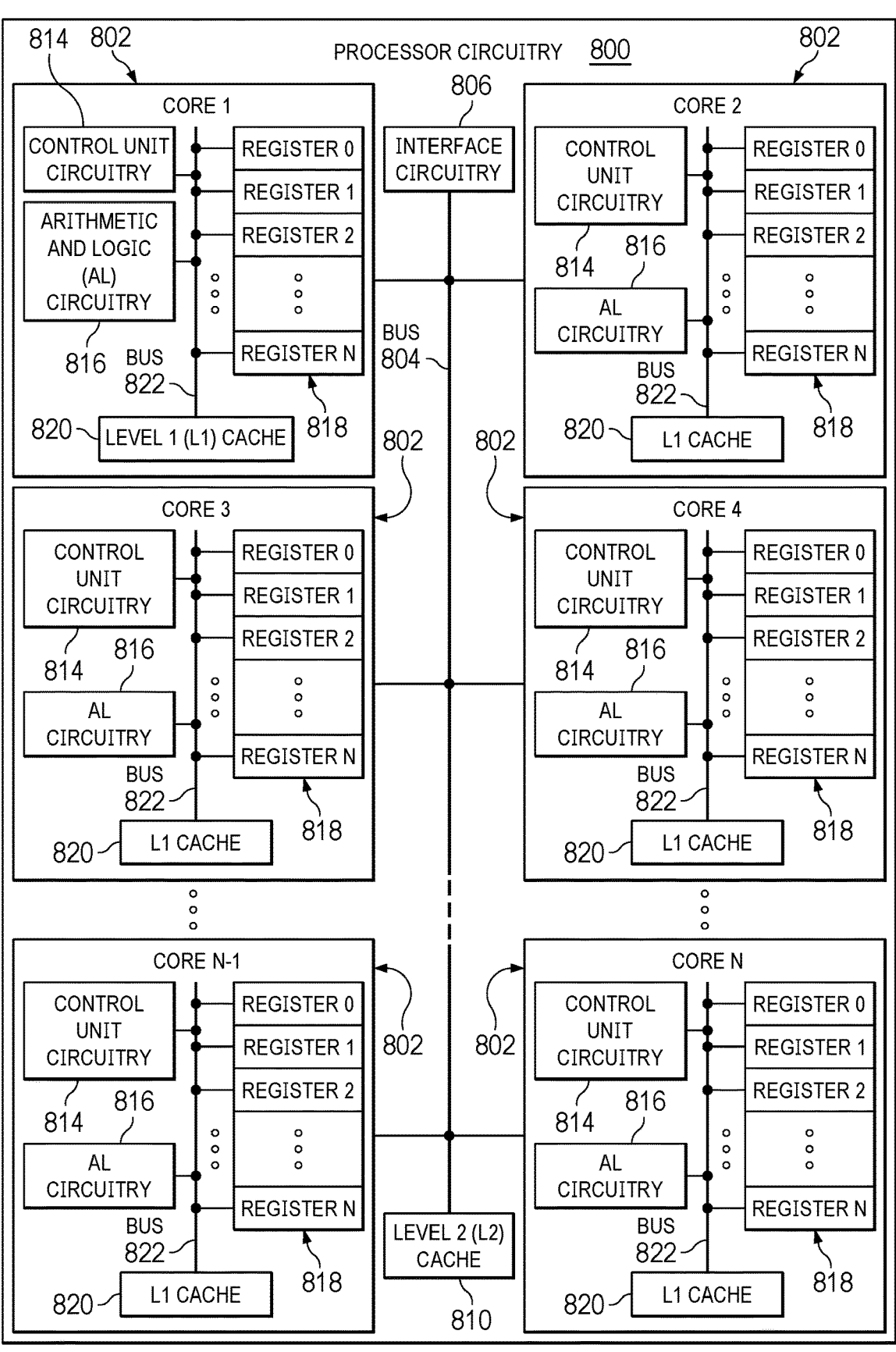
FIG. 8 is a block diagram of an example implementation of the programmable circuitry of FIG. 7.

FIG. 8 is a block diagram of an example implementation of the programmable circuitry 712 of FIG. 7. In this example, the programmable circuitry 712 of FIG. 7 is implemented by a microprocessor 800. For example, the microprocessor 800 may be a general-purpose microprocessor (e.g., general-purpose microprocessor circuitry). The microprocessor 800 executes some or all of the machine-readable instructions of the flowchart of FIG. 6 to effectively instantiate the circuitry of FIGS. 2-4 as logic circuits to perform operations corresponding to those machine-readable instructions. In some such examples, the circuitry of FIG. 4 is instantiated by the hardware circuits of the microprocessor 800 in combination with the machine-readable instructions. For example, the microprocessor 800 may be implemented by multi-core hardware circuitry such as a CPU, a DSP, a GPU, an XPU, etc. Although it may include any number of example cores 802 (e.g., 1 core), the microprocessor 800 of this example is a multi-core semiconductor device including N cores. The cores 802 of the microprocessor 800 may operate independently or may cooperate to execute machine readable instructions. For example, machine code corresponding to a firmware program, an embedded software program, or a software program may be executed by one of the cores 802 or may be executed by multiple ones of the cores 802 at the same or different times. In some examples, the machine code corresponding to the firmware program, the embedded software program, or the software program is split into threads and executed in parallel by two or more of the cores 802. The software program may correspond to a portion or all of the machine-readable instructions and/or operations represented by the flowchart of FIG. 6.

The cores 802 may communicate by a first example bus 804. In some examples, the first bus 804 may be implemented by a communication bus to effectuate communication associated with one(s) of the cores 802. For example, the first bus 804 may be implemented by at least one of an Inter-Integrated Circuit (I2C) bus, a Serial Peripheral Interface (SPI) bus, a PCI bus, or a PCIe bus. Additionally, or alternatively, the first bus 804 may be implemented by any other type of computing or electrical bus. The cores 802 may obtain data, instructions, and/or signals from one or more external devices by example interface circuitry 806. The cores 802 may output data, instructions, and/or signals to the one or more external devices by the interface circuitry 806. Although the cores 802 of this example include example local memory 820 (e.g., Level 1 (L1) cache that may be split into an L1 data cache and an L1 instruction cache), the microprocessor 800 also includes example shared memory 810 that may be shared by the cores (e.g., Level 2 (L2 cache)) for high-speed access to data and/or instructions. Data and/or instructions may be transferred (e.g., shared) by writing to and/or reading from the shared memory 810. The local memory 820 of each of the cores 802 and the shared memory 810 may be part of a hierarchy of storage devices including multiple levels of cache memory and the main memory (e.g., the main memory 714, 716 of FIG. 7). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 802 may be referred to as a CPU, DSP, GPU, etc., or any other type of hardware circuitry. Each core 802 includes control unit circuitry 814, arithmetic and logic (AL) circuitry (sometimes referred to as an ALU) 816, a plurality of registers 818, the local memory 820, and a second example bus 822. Other structures may be present. For example, each core 802 may include vector unit circuitry, single instruction multiple data (SIMD) unit circuitry, load/store unit (LSU) circuitry, branch/jump unit circuitry, floating-point unit (FPU) circuitry, etc. The control unit circuitry 814 includes semiconductor-based circuits structured to control (e.g., coordinate) data movement within the corresponding core 802. The AL circuitry 816 includes semiconductor-based circuits structured to perform one or more mathematic and/or logic operations on the data within the corresponding core 802. The AL circuitry 816 of some examples performs integer-based operations. In other examples, the AL circuitry 816 also performs floating-point operations. In yet other examples, the AL circuitry 816 may include first AL circuitry that performs integer-based operations and second AL circuitry that performs floating-point operations. In some examples, the AL circuitry 816 may be referred to as an Arithmetic Logic Unit (ALU).

The registers 818 are semiconductor-based structures to store data and/or instructions such as results of one or more of the operations performed by the AL circuitry 816 of the corresponding core 802. For example, the registers 818 may include vector register(s), SIMD register(s), general-purpose register(s), flag register(s), segment register(s), machine-specific register(s), instruction pointer register(s), control register(s), debug register(s), memory management register (s), machine check register(s), etc. The registers 818 may be arranged in a bank as shown in FIG. 8. Alternatively, the registers 818 may be organized in any other arrangement, format, or structure, such as by being distributed throughout the core 802 to shorten access time. The second bus 822 may be implemented by at least one of an I2C bus, a SPI bus, a PCI bus, or a PCIe bus.

Each core 802 and/or, more generally, the microprocessor 800 may include additional and/or alternative structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 800 is a semiconductor device fabricated to include many transistors interconnected to implement the structures described above in one or more integrated circuits (ICs) contained in one or more packages.

The microprocessor 800 may include and/or cooperate with one or more accelerators (e.g., acceleration circuitry, hardware accelerators, etc.). In some examples, accelerators are implemented by logic circuitry to perform certain tasks more quickly and/or efficiently than can be done by a general-purpose processor. Examples of accelerators include ASICs and FPGAs such as those described herein. A GPU, DSP and/or other programmable device can also be an accelerator. Accelerators may be on-board the microprocessor 800, in the same chip package as the microprocessor 800 and/or in one or more separate packages from the microprocessor 800.

Figure 9:
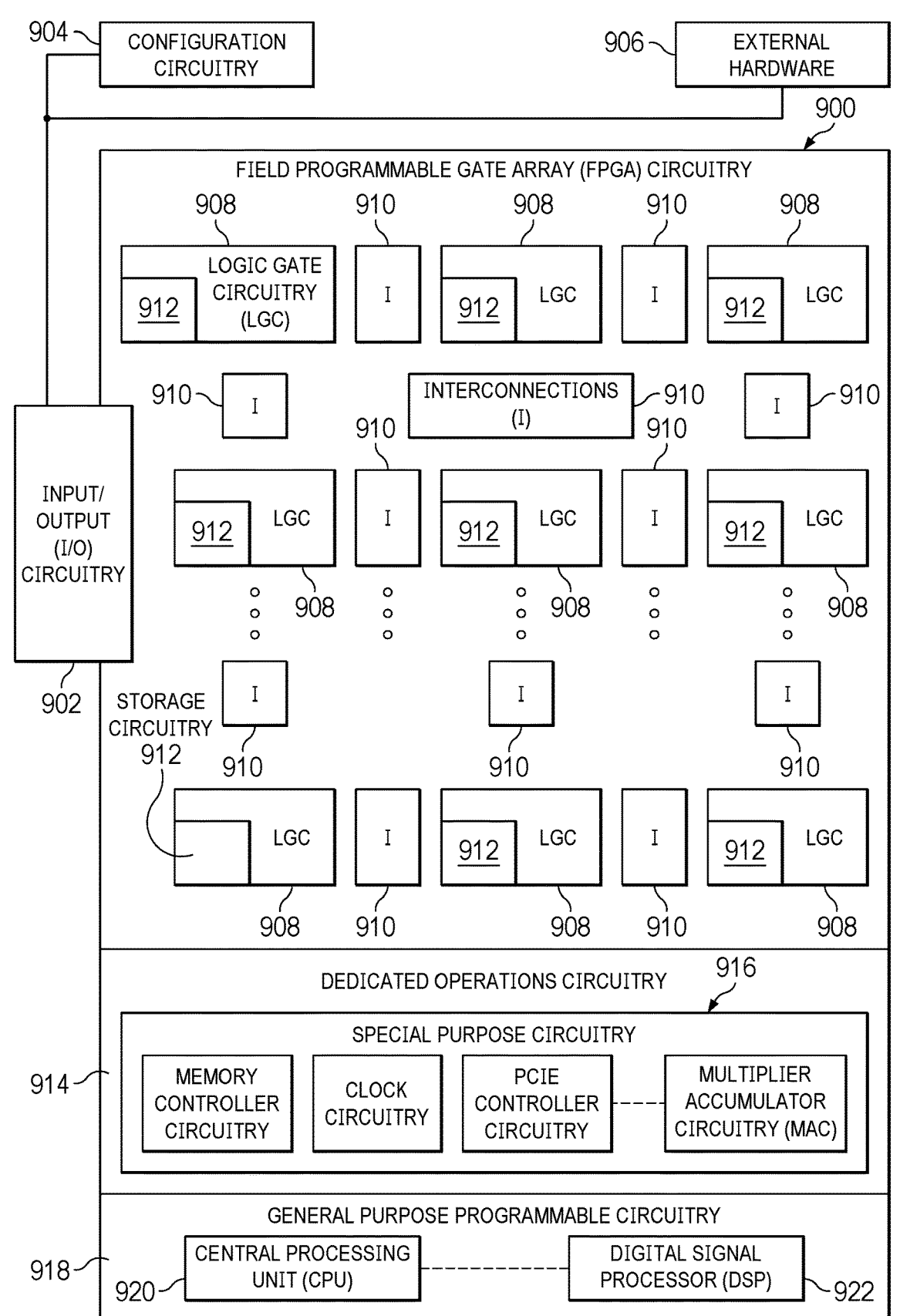
FIG. 9 is a block diagram of another example implementation of the programmable circuitry of FIG. 7.

FIG. 9 is a block diagram of another example implementation of the programmable circuitry 712 of FIG. 7. In this example, the programmable circuitry 712 is implemented by FPGA circuitry 900. For example, the FPGA circuitry 900 may be implemented by an FPGA. The FPGA circuitry 900 can be used, for example, to perform operations that could otherwise be performed by the example microprocessor 800 of FIG. 8 executing corresponding machine-readable instructions. However, once configured, the FPGA circuitry 900 instantiates the operations and/or functions corresponding to the machine-readable instructions in hardware and, thus, can often execute the operations/functions faster than they could be performed by a general-purpose microprocessor executing the corresponding software.

More specifically, in contrast to the microprocessor 800 of FIG. 8 described above (which is a general purpose device that may be programmed to execute some or all of the machine readable instructions represented by the flowchart of FIG. 6 but whose interconnections and logic circuitry are fixed once fabricated), the FPGA circuitry 900 of the example of FIG. 9 includes interconnections and logic circuitry that may be configured, structured, programmed, and/or interconnected in different ways after fabrication to instantiate, for example, some or all of the operations/functions corresponding to the machine readable instructions represented by the flowchart of FIG. 6. In particular, the FPGA circuitry 900 may be thought of as an array of logic gates, interconnections, and switches. The switches can be programmed to change how the logic gates are interconnected by the interconnections, effectively forming one or more dedicated logic circuits (unless and until the FPGA circuitry 900 is reprogrammed). The configured logic circuits enable the logic gates to cooperate in different ways to perform different operations on data received by input circuitry. Those operations may correspond to some or all of the instructions (e.g., the software and/or firmware) represented by the flowchart of FIG. 6. As such, the FPGA circuitry 900 may be configured and/or structured to effectively instantiate some or all of the operations/functions corresponding to the machine-readable instructions of the flowchart of FIG. 6 as dedicated logic circuits to perform the operations/functions corresponding to those software instructions in a dedicated manner analogous to an ASIC. Therefore, the FPGA circuitry 900 may perform the operations/functions corresponding to the some or all of the machine-readable instructions of FIG. 6 faster than the general-purpose microprocessor can execute the same.

In the example of FIG. 9, the FPGA circuitry 900 is configured and/or structured in response to being programmed (and/or reprogrammed one or more times) based on a binary file. In some examples, the binary file may be compiled and/or generated based on instructions in a hardware description language (HDL) such as Lucid, Very High-Speed Integrated Circuits (VHSIC) Hardware Description Language (VHDL), or Verilog. For example, a user (e.g., a human user, a machine user, etc.) may write code or a program corresponding to one or more operations/functions in an HDL; the code/program may be translated into a low-level language as needed; and the code/program (e.g., the code/program in the low-level language) may be converted (e.g., by a compiler, a software application, etc.) into the binary file. In some examples, the FPGA circuitry 900 of FIG. 9 may access and/or load the binary file. In such examples, the FPGA circuitry 900 of FIG. 9 is configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 900 of FIG. 9. In such an example, the binary file configures and/or structures the FPGA circuitry 900 of FIG. 9, or portion(s) thereof.

In some examples, the binary file is compiled, generated, transformed, and/or otherwise output from a uniform software platform utilized to program FPGAs. For example, the uniform software platform may translate first instructions (e.g., code or a program) that correspond to one or more operations/functions in a high-level language (e.g., C, C++, Python, etc.) into second instructions that correspond to the one or more operations/functions in an HDL. In some such examples, the binary file is compiled, generated, and/or otherwise output from the uniform software platform based on the second instructions. In some examples, the FPGA circuitry 900 of FIG. 9 may access and/or load the binary file. In such examples, the FPGA circuitry 900 of FIG. 9 is to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 900 of FIG. 9. In such an example, the binary file configures and/or structures the FPGA circuitry 900 of FIG. 9, or portion(s) thereof.

The FPGA circuitry 900 of FIG. 9, includes example input/output (I/O) circuitry 902 to obtain and/or output data to/from example configuration circuitry 904 and/or external hardware 906. For example, the configuration circuitry 904 may be implemented by interface circuitry that may obtain a binary file, which may be implemented by a bit stream, data, and/or machine-readable instructions, to configure the FPGA circuitry 900, or portion(s) thereof. In some such examples, the configuration circuitry 904 may obtain the binary file from a user, a machine (e.g., hardware circuitry (e.g., programmable or dedicated circuitry) that may implement an Artificial Intelligence/Machine Learning (AI/ML) model to generate the binary file), etc., and/or any combination(s) thereof. In some examples, the external hardware 906 may be implemented by external hardware circuitry. For example, the external hardware 906 may be implemented by the microprocessor 800 of FIG. 8.

The FPGA circuitry 900 also includes an array of example logic gate circuitry 908, a plurality of example configurable interconnections 910, and example storage circuitry 912. The logic gate circuitry 908 and the configurable interconnections 910 are configurable to instantiate one or more operations/functions that may correspond to at least some of the machine readable instructions of FIG. 6 and/or other desired operations. The logic gate circuitry 908 shown in FIG. 9 is fabricated in blocks or groups. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 908 to enable configuration of the electrical structures and/or the logic gates to form circuits to perform desired operations/functions. The logic gate circuitry 908 may include other electrical structures such as look-up tables (LUTs), registers (e.g., flip-flops or latches), multiplexers, etc.

The configurable interconnections 910 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 908 to program desired logic circuits.

The storage circuitry 912 of the illustrated example is structured to store result(s) of the one or more of the operations performed by corresponding logic gates. The storage circuitry 912 may be implemented by registers or the like. In the illustrated example, the storage circuitry 912 is distributed amongst the logic gate circuitry 908 to facilitate access and increase execution speed.

The example FPGA circuitry 900 of FIG. 9 also includes example dedicated operations circuitry 914. In this example, the dedicated operations circuitry 914 includes special purpose circuitry 916 that may be invoked to implement commonly used functions to avoid the need to program those functions in the field. Examples of such special purpose circuitry 916 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 900 may also include example general purpose programmable circuitry 918 such as an example CPU 920 and/or an example DSP 922. Other general purpose programmable circuitry 918 may additionally or alternatively be present such as a GPU, an XPU, etc., that can be programmed to perform other operations.

Although FIGS. 8 and 9 illustrate two example implementations of the programmable circuitry 712 of FIG. 7, many other approaches are contemplated. For example, FPGA circuitry may include an on-board CPU, such as one or more of the example CPU 920 of FIG. 8. Therefore, the programmable circuitry 712 of FIG. 7 may additionally be implemented by combining at least the example microprocessor 800 of FIG. 8 and the example FPGA circuitry 900 of FIG. 9. In some such hybrid examples, one or more cores 802 of FIG. 8 may execute a first portion of the machine readable instructions represented by the flowchart of FIG. 6 to perform first operation(s)/function(s), the FPGA circuitry 900 of FIG. 9 may be configured and/or structured to perform second operation(s)/function(s) corresponding to a second portion of the machine readable instructions represented by the flowchart of FIG. 6, and/or an ASIC may be configured and/or structured to perform third operation(s)/function(s) corresponding to a third portion of the machine readable instructions represented by the flowchart of FIG. 6.

It should be understood that some or all of the circuitry of FIGS. 2-4 may, thus, be instantiated at the same or different times. For example, same and/or different portion(s) of the microprocessor 800 of FIG. 8 may be programmed to execute portion(s) of machine-readable instructions at the same and/or different times. In some examples, same and/or different portion(s) of the FPGA circuitry 900 of FIG. 9 may be configured and/or structured to perform operations/functions corresponding to portion(s) of machine-readable instructions at the same and/or different times.

In some examples, some or all of the circuitry of FIGS. 2-4 may be instantiated, for example, in one or more threads executing concurrently and/or in series. For example, the microprocessor 800 of FIG. 8 may execute machine readable instructions in one or more threads executing concurrently and/or in series. In some examples, the FPGA circuitry 900 of FIG. 9 may be configured and/or structured to carry out operations/functions concurrently and/or in series. Moreover, in some examples, some or all of the circuitry of FIG. 4 may be implemented within one or more virtual machines and/or containers executing on the microprocessor 800 of FIG. 8.

In some examples, the programmable circuitry 712 of FIG. 7 may be in one or more packages. For example, the microprocessor 800 of FIG. 8 and/or the FPGA circuitry 900 of FIG. 9 may be in one or more packages. In some examples, an XPU may be implemented by the programmable circuitry 712 of FIG. 7, which may be in one or more packages. For example, the XPU may include a CPU (e.g., the microprocessor 800 of FIG. 8, the CPU 920 of FIG. 9, etc.) in one package, a DSP (e.g., the DSP 922 of FIG. 9) in another package, a GPU in yet another package, and an FPGA (e.g., the FPGA circuitry 900 of FIG. 9) in still yet another package.

In this description, a component, element, and/or device may be described as a switch. Such a switch and/or switches may be embodied, described, and/or illustrated using transistors. For example, the switches 220, 225, 230, 240, 245, 250 of FIGS. 2 and/or 3 may be embodied, described, and/or illustrated as transistors. Such a transistor(s) may be one or more of an n-channel field-effect transistor (FET), an n-channel metal-oxide semiconductor field-effect transistor (MOSFET), an n-channel insulated-gate bipolar transistor (IGBT), an n-channel junction field effect transistor (JFET), an NPN bipolar junction transistor (BJT) and/or, with slight modifications, a p-type equivalent device.

In this description, the term "and/or" (when used in a form such as A, B and/or C) refers to any combination or subset of A, B, C, such as: (a) A alone; (b) B alone; (c) C alone; (d) A with B; (e) A with C; (f) B with C; and (g) A with B and with C. Also, as used herein, the phrase "at least one of A or B" (or "at least one of A and B") refers to implementations including any of: (a) at least one A; (b) at least one B; and (c) at least one A and at least one B.

The term "couple" is used throughout the specification. The term may cover connections, communications, or signal paths that enable a functional relationship consistent with this description. For example, if device A provides a signal to control device B to perform an action, in a first example device A is coupled to device B, or in a second example device A is coupled to device B through intervening component C if intervening component C does not substantially alter the functional relationship between device A and device B such that device B is controlled by device A via the control signal provided by device A.

Numerical identifiers such as "first", "second", "third", etc. are used merely to distinguish between elements of substantially the same type in terms of structure and/or function. These identifiers as used in the detailed description do not necessarily align with those used in the claims.

A device that is "configured to" perform a task or function may be configured (e.g., programmed and/or hardwired) at a time of manufacturing by a manufacturer to perform the function and/or may be configurable (or re-configurable) by a user after manufacturing to perform the function and/or other additional or alternative functions. The configuring may be through firmware and/or software programming of the device, through a construction and/or layout of hardware components and interconnections of the device, or a combination thereof.

As used herein, the terms "terminal", "node", "interconnection", "pin" and "lead" are used interchangeably. Unless specifically stated to the contrary, these terms are generally used to mean an interconnection between or a terminus of a device element, a circuit element, an integrated circuit, a device or other electronics or semiconductor component.

A circuit or device that is described herein as including certain components may instead be adapted to be coupled to those components to form the described circuitry or device. For example, a structure described as including one or more semiconductor elements (such as transistors), one or more passive elements (such as resistors, capacitors, and/or inductors), and/or one or more sources (such as voltage and/or current sources) may instead include only the semiconductor elements within a single physical device (e.g., a semiconductor die and/or integrated circuit (IC) package) and may be adapted to be coupled to at least some of the passive elements and/or the sources to form the described structure either at a time of manufacture or after a time of manufacture, for example, by an end-user and/or a third-party.

Circuits described herein are reconfigurable to include the replaced components to provide functionality at least partially similar to functionality available prior to the component replacement. Components shown as resistors, unless otherwise stated, are generally representative of any one or more elements coupled in series and/or parallel to provide an amount of impedance represented by the shown resistor. For example, a resistor or capacitor shown and described herein as a single component may instead be multiple resistors or capacitors, respectively, coupled in parallel between the same nodes. For example, a resistor or capacitor shown and described herein as a single component may instead be multiple resistors or capacitors, respectively, coupled in series between the same two nodes as the single resistor or capacitor. While certain elements of the described examples are included in an integrated circuit and other elements are external to the integrated circuit, in other example embodiments, additional or fewer features may be incorporated into the integrated circuit. In addition, some or all of the features illustrated as being external to the integrated circuit may be included in the integrated circuit and/or some features illustrated as being internal to the integrated circuit may be incorporated outside of the integrated. As used herein, the term "integrated circuit" means one or more circuits that are: (i) incorporated in/over a semiconductor substrate; (ii) incorporated in a single semiconductor package; (iii) incorporated into the same module; and/or (iv) incorporated in/on the same printed circuit board.

Uses of the phrase "ground" in the foregoing description include a chassis ground, an Earth ground, a floating ground, a virtual ground, a digital ground, a common ground, and/or any other form of ground connection applicable to, or suitable for, the teachings of this description. Unless otherwise stated, "about," "approximately," or "substantially" preceding a value means +/−10 percent of the stated value, or, if the value is zero, a reasonable range of values around zero.

Example systems, apparatus, articles of manufacture, and methods have been described that improve an LED supply voltage based on headroom voltages of LEDs. Described systems, apparatus, articles of manufacture, and methods improve the efficiency of using a computing device by reducing power consumption in driving LEDs. Described systems, apparatus, articles of manufacture, and methods are accordingly directed to one or more improvement(s) in the operation of a machine such as a computer or other electronic and/or mechanical device.

Modifications are possible in the described embodiments, and other embodiments are possible, within the scope of the claims.

What is claimed is:

1. A system comprising:
a first light emitting diode (LED) having a first terminal and a second terminal;
a second LED having a first terminal and a second terminal, the first terminal of the second LED coupled to the first terminal of the first LED;
driver circuitry having a first terminal and a second terminal, the first terminal of the driver circuitry coupled to the second terminal of the first LED, the second terminal of the driver circuitry coupled to the second terminal of the second LED;
a first switch having a first terminal and a second terminal, the first terminal of the first switch coupled to the second terminal of the first LED and the first terminal of the driver circuitry;
a second switch having a first terminal and a second terminal, the first terminal of the second switch coupled to the second terminal of the second LED and the second terminal of the driver circuitry;
sense control circuitry having a first terminal, a second terminal, and a third terminal, the first terminal of the sense control circuitry coupled to the second terminal of the first switch, the second terminal of the sense control circuitry coupled to the second terminal of the second switch, the sense control circuitry configured to determine a headroom voltage of the driver circuitry for the first and second LEDs; and
power converter having a control terminal and an output, the control terminal of the power converter coupled to the third terminal of the sense control circuitry, the output of the power converter coupled to the first terminal of the first LED and the first terminal of the second LED;
wherein the sense control circuitry further includes:
an analog to digital converter (ADC) having a first terminal and a second terminal, the first terminal of the ADC configured to be coupled to the second terminal of the first switch and the second terminal of the second switch; and
comparison circuitry having a first terminal, a second terminal, and a third terminal, the first terminal of the comparison circuitry coupled to the second terminal of the ADC, the second terminal of the comparison circuitry configured to be coupled to the third terminal of the comparison circuitry.

2. The system of claim 1, further comprising a photodiode configured to be optically coupled to at least one of the first LED or the second LED.

3. The system of claim 1, wherein the driver circuitry includes:
a third switch having a first terminal and a second terminal, the first terminal of the third switch coupled to the second terminal of the first LED; and
a fourth switch having a first terminal and a second terminal, the first terminal of the fourth switch coupled to the second terminal of the second LED, the second terminal of the fourth switch coupled to the second terminal of the third switch.

4. A system comprising:
a first light emitting diode (LED) having a first terminal and a second terminal;
a second LED having a first terminal and a second terminal, the first terminal of the second LED coupled to the first terminal of the first LED;
driver circuitry having a first terminal and a second terminal, the first terminal of the driver circuitry coupled to the second terminal of the first LED, the second terminal of the driver circuitry coupled to the second terminal of the second LED;
a first switch having a first terminal and a second terminal, the first terminal of the first switch coupled to the second terminal of the first LED and the first terminal of the driver circuitry;
a second switch having a first terminal and a second terminal, the first terminal of the second switch coupled to the second terminal of the second LED and the second terminal of the driver circuitry;
sense control circuitry having a first terminal, a second terminal, and a third terminal, the first terminal of the sense control circuitry coupled to the second terminal of the first switch, the second terminal of the sense control circuitry coupled to the second terminal of the second switch, the sense control circuitry configured to determine a headroom voltage of the driver circuitry for the first and second LEDs; and
power converter having a control terminal and an output, the control terminal of the power converter coupled to the third terminal of the sense control circuitry, the output of the power converter coupled to the first terminal of the first LED and the first terminal of the second LED;
wherein the driver circuitry includes:
a third switch having a first terminal and a second terminal, the first terminal of the third switch coupled to the second terminal of the first LED; and a fourth switch having a first terminal and a second terminal, the first terminal of the fourth switch coupled to the second terminal of the second LED, the second terminal of the fourth switch coupled to the second terminal of the third switch; and wherein the first switch, the second switch, the third switch, and the fourth switch further have a control terminal, further comprising switch control circuitry having a first terminal and a second terminal, the first terminal of the switch control circuitry coupled to the control terminal of the first switch and the third switch, the second terminal of the switch control circuitry coupled to the control terminal of the second switch and the fourth switch.

5. The system of claim 4, wherein the sense control circuitry including:

an analog to digital converter (ADC) having a first terminal and a second terminal, the first terminal of the ADC configured to be coupled to the second terminal of the first switch and the second terminal of the second switch; and comparison circuitry having a first terminal, a second terminal, and a third terminal, the first terminal of the comparison circuitry coupled to the second terminal of the ADC, the second terminal of the comparison circuitry configured to be coupled to the third terminal of the comparison circuitry.

6. The system of claim 1, wherein the power converter is a buck-boost converter.

7. An apparatus comprising:

driver circuitry having a first terminal and a second terminal; and voltage control circuitry having a first terminal and a second terminal, the first terminal of the voltage control circuitry coupled to the first terminal of the driver circuitry, the second terminal of the voltage control circuitry coupled to the second terminal of the driver circuitry, the voltage control circuitry configured to supply a supply voltage;

wherein the voltage control circuitry comprises:

a first switch having a terminal coupled to the first terminal of the driver circuitry;

a second switch having a terminal coupled to the second terminal of the driver circuitry; and sense control circuitry including:

an analog to digital converter (ADC) having a first terminal and a second terminal, the first terminal of the ADC configured to be coupled to the second terminal of the first switch and the second terminal of the second switch; and comparison circuitry having a first terminal, a second terminal, and a third terminal, the first terminal of the comparison circuitry coupled to the second terminal of the ADC, the second terminal of the comparison circuitry configured to be coupled to the third terminal of the comparison circuitry.

8. The apparatus of claim 7, further comprising:

a first light emitting diode (LED) having a first terminal and a second terminal, the second terminal of the first LED coupled to the first terminal of the driver circuitry and the first terminal of the voltage control circuitry; and a second LED having a first terminal and a second terminal, the first terminal of the second LED coupled to the first terminal of the first LED, the second terminal of the second LED coupled to the second terminal of the driver circuitry and the second terminal of the voltage control circuitry.

9. The apparatus of claim 7, wherein the driver circuitry including:

a third switch having a first terminal and a second terminal, the first terminal of the third switch coupled to the first terminal of the voltage control circuitry; and a fourth switch having a first terminal and a second terminal, the first terminal of the fourth switch coupled to the second terminal of the voltage control circuitry, the second terminal of the second switch coupled to the second terminal of the first switch.

10. The apparatus of claim 9, wherein the driver circuitry further includes current source circuitry having a terminal coupled to the second terminal of the first switch and the second terminal of the second switch.

11. The apparatus of claim 7, wherein the voltage control circuitry further includes a power converter having a first terminal coupled to the sense control circuitry, and a second terminal configured to be coupled to a light emitting diode (LED).

12. The apparatus of claim 11, wherein the power converter is a buck-boost converter.

13. A device comprising:

driver circuitry having a first terminal and a second terminal, the driver circuitry to source a current from one of the first terminal or the second terminal; and voltage control circuitry configured to:

determine a first headroom voltage corresponding to a current to flow through the first terminal of the driver circuitry;

determine a second headroom voltage corresponding to a current flowing through the second terminal of the driver circuitry;

determine a modified LED supply voltage based on the first headroom voltage and the second headroom voltage; and determine the first headroom voltage based on a voltage difference across the driver circuitry when a current is flowing through one of the terminals of the driver circuitry.

14. The device of claim 13, wherein the voltage control circuitry is further configured to configure a power converter to supply a voltage corresponding to the modified LED supply voltage.

15. The device of claim 13, wherein the voltage control circuitry is further configured to determine the modified LED supply voltage based on a minimum headroom voltage of the driver circuitry.

16. The device of claim 13, further including switch control circuitry configured to control a first switch and a second switch of the driver circuitry, a current to flow through a specific one of the first or the second terminal of the driver circuitry responsive to the switch control circuitry.

17. The device of claim 13, wherein the driver circuitry is configured to source a first current from the first terminal for a first time and a second current from the second terminal for a second time, a first LED to emit light responsive to the first current, a second LED to emit light responsive to the second current.

18. The device of claim 17, wherein the voltage control circuitry is configured to determine the modified LED supply voltage based on the first headroom voltage, the second headroom voltage, the first current, and the second current.

19. The device of claim 17, wherein the voltage control circuitry is configured to determine the first headroom voltage at the first time and the second headroom voltage at the second time.

20. A device comprising:

driver circuitry having a first terminal and a second terminal, the driver circuitry to source a current from one of the first terminal or the second terminal; and voltage control circuitry configured to:

determine a first headroom voltage corresponding to a current to flow through the first terminal of the driver circuitry;

determine a second headroom voltage corresponding to a current flowing through the second terminal of the driver circuitry;

determine a modified LED supply voltage based on the first headroom voltage and the second headroom voltage; and switch control circuitry configured to:

control a first switch and a second switch of the driver circuitry, a current to flow through a specific one of the first or the second terminal of the driver circuitry responsive to the switch control circuitry; and control a third switch and a fourth switch of the voltage control circuitry to determine the first headroom voltage or the second headroom voltage.

\* \* \* \* \*